(12) United States Patent
Collin

(10) Patent No.: US 6,399,105 B1
(45) Date of Patent: *Jun. 4, 2002

(54) SEA CUCUMBER CAROTENOID LIPID FRACTION PRODUCTS AND METHODS OF USE

(76) Inventor: Peter Donald Collin, P.O. Box 172, Sunset, ME (US) 04683

( * ) Notice: Subject to any disclaimer, the term of this patent is extended or adjusted under 35 U.S.C. 154(b) by 0 days.

This patent is subject to a terminal disclaimer.

(21) Appl. No.: 09/622,220
(22) PCT Filed: Jan. 20, 1999
(86) PCT No.: PCT/US99/01179
§ 371 (c)(1), (2), (4) Date: Aug. 15, 2000
(87) PCT Pub. No.: WO99/37314
PCT Pub. Date: Jul. 29, 1999

(51) Int. Cl.⁷ ............................................. A61K 35/37
(52) U.S. Cl. .................. 424/550; 424/548; 424/551; 426/805; 514/558; 514/559; 514/560; 557/18; 557/221
(58) Field of Search ................ 424/548, 550, 424/551; 554/18, 221; 426/805; 514/558, 559, 560

(56) References Cited

U.S. PATENT DOCUMENTS

| 4,900,815 A | 2/1990 | Tanaka et al. |
| 5,519,010 A | 5/1996 | Fan et al. |
| 6,055,936 A | * 5/2000 | Collin ............... 554/18 |

FOREIGN PATENT DOCUMENTS

| CA | 2026990 | 6/1996 |
| EP | 0 495 116 A1 | 7/1992 |
| EP | 0 495 116 B1 | 7/1992 |
| EP | 0 408 770 B1 | 6/1996 |

OTHER PUBLICATIONS

Anisimov, M.M. et al. "Comparative Study of Cytotoxic Activity of Triterpene Glycosides from Marine Organisms", *Toxicon.*, 1980; 18:221–223.

Colliec, S. et al. "Anticoagulant Properties of a Fucoidan Fraction", *Thrombosis Research*, 1991; 64:143–154.

Eylers, J.P. "Ion–Dependent Viscosity of Holothurian Body Wall and its Implications for the Functional Morphology of Echinoderms", *J. exp. Biol.*, 1982; 99:1–8.

Findlay, J.A. et al. "Frondogenin, A New Aglycone From the Sea Cucumber *Cucumaria Frondosa*", *Journal of Natural Products*, Mar.–Apr. 1984; 47(2):320–324.

Kalyani, G.A. et al. "Holothurin—A Review", *Indian J. Nat. Prod.*, 1988; 4(2):3–8.

Matsumura, T. et al. "Disaggregation of Connective Tissue: Preparation of Fibrous Components from Sea Cucumber Body Wall and Calf Skin", *J. Biochem.*, 1973; 73:155–162.

Mauray, S. et al. "Venous Antithrombotic and Anticoagulant Activities of a Fucoïdan Fraction", *Thrombosis and Haemostasis*, 1995; 74(5):1280–5.

McLellan, D.S. et al. "Anticoagulants from marine algae", *Blood Coagulation and Fibrinolysis*, 1992; 3:69–77.

Miyamoto, T. et al. "Six Newly Identified Biologically Active Triterpenoid Glycoside Sulfates from the Sea Cucumber *Cucumaria echinata*", *Liebigs Ann. Chem.*, 1990; pp. 453–460.

(List continued on next page.)

*Primary Examiner*—Deborah D. Carr
(74) *Attorney, Agent, or Firm*—Rothwell, Figg, Ernst & Manbeck

(57) ABSTRACT

Methods and compositions of matter are described for treatment of inflammatory autoimmune and other diseases by administration of lipid fractions of sea cucumber tissue. Compositions of matter useful for inclusion in aquatic and human diets are also disclosed.

45 Claims, 9 Drawing Sheets

OTHER PUBLICATIONS

Mourão, P.A.S. et al., "Structure and Anticoagulant Activity of a Fucosylated Chondroitin Sulfate from Echinoderm", *The Journal of Biological Chemistry*, Sep. 27, 1996; 274(39):23973–23984.

Mourão, P.A.S. et al., "Sulfated Polysaccharides from Echinoderms Reveal Unique Structures and New Potential as Bioactive Polymers", *Trends in Glycoscience and Glycotechnology*, May 1995; 7(35):235–246.

Mulloy, B. et al. "Sulfated Fucans from Echinoderms Have a Regular Tetrasaccharide Repeating Unit Defined by Specific Patterns of Sulfation at the 0–2 and 0–4 Positions", *Journal of Biological Chemistry*, Sep. 2, 1994; 269(35):22113–22123.

Nagase, H. et al. "Depolymerized Holothurian Glycosaminoglycan With Novel Anticoagulant Actions: Antithrombin III—and Heparin Cofactor II–Independent Inhibition of Factor X Activation by Factor IXa—Factor VIIIa Complex and Heparin Cofactor II–Dependent Inhibition of Thrombin", *Blood*, Mar. 15, 1995; 85(6):1527–1534.

Pettit, G.R. et al. "Antineoplastic Agents XLV: Sea Cucumber Cytotoxic Saponins", *Journal of Pharmaceutical Sciences*, Oct. 1976; 65(10):1558–9.

Rodriguez, J. et al. "Holothurinosides: New Antitumour Non Sulphated Triterpenoid Glycosides from the Sea Cucumber *Holothuria Forskalii*", *Tetrahedron*, 1991; 47(26):4753–4762.

Santhakumari, G. et al. "Antimitotic Effects of Holothurin", *Cytologia*, 1988; 53:163–168.

Suzuki, N. et al. "Antithrombotic and Anticoagulant Activity of Depolymerized Fragment of the Glycosaminoglycan Extracted from *Stichopus japonicus* Selenka", *Thrombosis and Haemostasis*, 1991; 65(4):369–373.

Nishino, T. et al. "Antithrombin Activity of a Fucan Sulfate from the Brown Seaweed *Ecklonia kurome*", *Thrombosis Research*; 1991; 62:765–773.

Vieira, R.P. et al. "Occurrence of a Unique Fucose–branched Chondroitin Sulfate in the Body Wall of a Sea Cucumber", *The Journal of Biological Chemistry*, Dec. 5, 1988; 263(34):18176–18183.

Vieira, R.P. et al. "Structure of a Fucose–branched Chondroitin Sulfate from Sea Cucumber", *The Journal of Biological Chemistry*, Jul. 25, 1991; 266(21):13530–13536.

\* cited by examiner

SEA CUCUMBER CAROTENOID LIPID FRACTION PRODUCTS AND METHODS OF USE

This application is a 371 of PCT/US 99/01179 filed Jan. 20, 1999.

FIELD OF THE INVENTION

This patent relates to the general field of therapeutic products and methods to inhibit certain disease states related to the general medical field of human and veterinary pharmacology wherein the activation of the lipoxygenase pathways contribute to the pathological condition. Agents which inhibit or modulate the 5-lipoxygenase or 12-lipoxygenase pathways are known to be useful in the medical arts. Agents with little or no toxicity that inhibit systemic or dermatological inflammations are useful in the healing arts. This patent also relates to the field of pigmented agents useful in the aquaculture industry, wherein pigmented ingredients must be incorporated into aquatic feeds in order to bring about a deposition of color either in the flesh of the animal, or on the skin or shell thereof.

More particularly, the present invention concerns certain novel lipids derived from the class Holothuridea, or sea cucumber, and especially, the *Cucumaria frondosa* variety found in Maine and the North Atlantic. Any species of sea cucumber parts will suffice for raw material from which to extract the compounds of the present invention. The oils of such sea cucumbers from any species can be used for pigmentation of aquatic species by incorporation into feeds, as well as for the treatment or amelioration of diseases in which products of lipoxygenase enzyme activity or the reaction of leukotrienes contribute to the pathological condition. That is, the novel lipids derived from any class or species of sea cucumber inhibit lipoxygenase enzymes and/ or bind leukotriene receptors. Lipoxygenase enzymes are well known in the arachidonic acid cascade. These oils, designated RED OIL and GOLD OIL, can be used as-is for immunosuppressive purposes and also provide raw materials from which to derive ingredients of immunosuppressive drugs suitable to ameliorate immune responses due to organ transplant or autoimmune response in diseases such as lupus or rheumatoid arthritis. These oils or derivatives thereof from molecular distillation are suitable 'as-is' or may be further fractionated by means known to the arts and can be used to reduce, suppress, inhibit, or prevent unwanted immune responses, e.g., in humans or animals requiring immunosuppression. Examples of such situations include. but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents. The subject invention further pertains to pharmaceutical compositions containing these compounds. These oils are also shown by the present invention to inhibit angiogenesis, as shown in the chick chorioallantoic membrane assay (Knighton et al., 1977). The pigmented oil, designated for purposes of this patent as RED OIL. has been shown to contain surprising amounts of the carotenoids, canthaxanthin and astaxanthin, and is suitable for adding to commercial fish feeds in order to bring color deposition to the flesh or skin of particular species in need of same.

BACKGROUND

The present invention relates to novel compounds, pharmaceutical compositions and methods of use for the treatment of diseases in which the 5- and 12-lipoxygenase activity contributes to the pathological condition. The present invention also relates to products derived from the lipid fractions of sea cucumber tissue which ameliorate immune responses and which can also be incorporated into aquatic diets for the purpose of imparting color to the flesh or skin of such fish or shrimp. Although there have been reports in the literature concerning marine lipids from certain fish in the treatment of various arthritis related diseases, sea cucumber lipids have never been included in any studies, nor is there any evidence that the inflammation inhibitory mechanisms known of vertebrate fishes in mammalian systems is relevant to this invention (DeLuca et al., 1995). It is also known that certain marine sponges and ascidians possess immunomodulatory or immunosuppressive activities, but there are no reports in the field of marine pharmacology that sea cucumber lipids have been discovered to possess any such inhibitory activities useful in the medical arts (Konig and Wright, 1995).

More particularly, the compounds defined below inhibit the 5-lipoxygenase pathway and the 12-lipoxygenase pathway in mammals. Lipoxygenase pathway products such as the leukotrienes $B_4$, $C_4$, $D_4$ and $E_4$, 5-hydroxyeicosatetraenoic acid, 5-hydroperoxyeicosatetraenoic acid and 12-hydroxyeicosatetracnoic acid are related to the above described conditions. Specific conditions for use of the present novel lipoxygenase-inhibiting compounds, pharmaceutical compositions thereof and the novel method of use in accordance with the present invention include allergy; asthma; arthritis; skin disorders including psoriasis, a topic dermatitis and acne; inflammation-including inflammatory bowel diseases or pain; various cancers including prostate, lung, colorectal, and skin; and cardiovascular disorders including myocardial ischemia and infarction, angina, arrhythmias, stroke, migraine and atherosclerosis.

The compounds of the present invention are derived from the lipid fractions of sea cucumber of any species or subphyla; from the de-pigmented fraction of such lipid fraction; from the molecular distillation phases as are known to those skilled in the arts; or from the chromatographic column separations of same; from the epidermal. dermal, anterior, posterior, or intestinal mass including respiratory trees, gonads, cuverian tubules or polian vesicles of any sea cucumber.

Sea cucumbers of various species provide medically active fractions useful to die healing arts. U.S. Pat. No. 5.519,010 teaches that a de-polymerized polysaccharide is useful as an anti-coagulant. U.S. Pat. No. 5,770,205 by Collin teaches that sea cucumber tissues extracted by various methods possess anti-inflammatory activity useful in the human and veterinary medical arts. Glycosides from sea cucumber organs have been shown to contain anti-cancer agents (Miyamoto et al., 1990). None of the above describe a lipid from sea cucumber which inhibits any lipoxygenase pathway, nor inflammation, nor describes any utility of such sea cucumber-derived agents to inhibit pathological disease conditions in which lipoxygenase products, isomers, or metabolites contribute to such condition. Nor do any of the above patents present any art wherein such lipids provide an immunomodulatory activity in a mammal.

The present invention teaches that both the pigment-rich lipid materials and the de-pigmented lipid materials and the Light Phases recovered from molecular distillation of any of the pigmented or de-pigmented sea cucumber lipid materials are able to inhibit the 5-lipoxygenase enzyme activity in human neutrophils and the 12-lipoxygenase enzyme in human platelets.

There are currently many patents describing agents which purport to inhibit the leukotriene and 5-lipoxygenase and 12-lipoxygenase pathways in mammals. Some of these compounds are effective, and some have toxic side-effects or cannot be cost-effectively produced. It is an object of the present invention that the production of sea cucumber oils and their derivatives which can be incorporated into ointments, suppositories, and embodied into orally administered or injected medicines or into medicine administered by other means, provides a cost effective and readily available means to modulate the leukotriene pathway in mammals and thus will contribute to the therapeutic treatment of such diseases as cancer, psoriasis, atopic dermatitis, etc. in which leukotrienes, $LTB_4$, 5-HETE and 12-HETE contribute to the pathological condition.

OBJECTS OF THE PRESENT INVENTION

Therapeutic application of the new compounds and compositions containing them can be contemplated to be accomplished by any suitable therapeutic method and technique presently or prospectively known to those skilled in the art. Further, the compounds of the present invention have use as starting materials or intermediates for the preparation of other useful compounds and compositions exhibiting more potent activity.

It is an object of the present invention to provide to the arts pharmaceutical compositions comprising, as active ingredients, an effective amount of one or more of the novel compounds herein described. An object of the present invention is to provide to the art new compounds which are useful as immunomodulatory agents through their inhibitory activities of the lipoxygenase pathways in mammals and through their inhibitory activities of the lymphocyte proliferation pathways of the mammalian immune system, as well as ingredients which are useful in aquatic diets for the pigmentation of marine life. Molecular distillation or other separatory technique fractions comprising the LIGHT PHASES so called of the extracted sea cucumber oils native to sea cucumber tissues have been shown to be inhibitory of the lipoxygenase pathways. Also, the HEAVY PHASES from molecular distillation of these same oils show similar activities. Isolations of more active moieties of these pathways can be produced through column chromatography, for example, or other methods known to those skilled in the lipid biochemistry arts. Therefore it is an object of the present invention to provide a raw material and active intermediates for such isolations if more potent or specific fractions are desired.

The compounds of this invention inhibit 5-lipoxygenase and 12-lipoxygenase activity in mammals, which inhibitory activity has been associated with antiallergic, anti-inflammatory and antihyperproliferative activity. The compounds of the invention are thus useful for the treatment of allergic diseases as discussed above, inflammatory diseases of the epithelium, heart-burn, cancer and hyperproliferative skin diseases. They have also been shown to inhibit lymphocyte proliferation in human blood.

The inflammatory diseases which may be treated include arthritis, bursitis, tendinitis, gout and inflammatory bowel disease.

"Hyperproliferative skin disease" means any condition, a symptom of which is accelerated skin cell production, flaking, scales or papular lesions. Examples of hyperproliferative skin diseases include, for example, psoriasis, lichenified eczema, dandruff and the like.

The compounds of this invention can be administered in any number of conventional dosage forms, e.g. topical, oral, parenteral, rectal, transdermal, inhalation and the like. Oral or rectal dosage forms include capsules, tablets, pills, powders, cachets and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g. of the conventional patch or matrix type) and the like and are preferred for treating hyperproliferative skin diseases.

The formulations and pharmaceutical compositions contemplated by the above dosage forms can be prepared with conventional pharmaceutically acceptable excipients and additives using conventional techniques. Such pharmaceutically acceptable excipients and additives are intended to include carriers, binders, flavorings, buffers, thickeners, color agents, stabilizing agents, emulsifying agents, dispersing agents, suspending agents, perfumes, preservatives, lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or can be used in finely divided powder form without excipients for inclusion into capsules. Similarly, cachets are included as are liposomes as are known to those skilled in the arts.

Liquid form preparations include solutions, suspensions and emulsions. As an example, it may be mentioned of water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in the oil form within an emulsifier such as TWEEN-80 as is known in the industry familiar with oil/water emulsions.

Formulations for topical application, e.g., for use in treating hyperproliferative skin diseases, may include the above liquid forms, as well as creams, aerosols, sprays, dusts wherein the oil is admixed with a suitable carrier, lotions and ointments which are prepared by combining the active ingredient according to this invention with conventional pharmaceutical acceptable diluents and carriers commonly used in topical formulations. Ointments and creams may, for example, be formulated with an aqueous or oily base with the addition of suitable thickening and/or gelling agents. Such bases may, for example, include water and/or an oil such as liquid paraffin or beeswax or a vegetable oil such as peanut oil or castor oil. Thickening agents which may be used according to the nature of the base include soft waxes, aluminum stearate, cetostearyl alcohol, propylene glycol, polyethylene glycol, woolfat, hydrogenated lanolin, etc.

Lotions may be formulations with an aqueous or oil base and will, in general, also include one or more pharmaceutically acceptable stabilizing agents, emulsifying agents, dispersing agents, suspending agents, thickening agents, coloring agents, perfumes and the like.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobials, particularly antibiotics, anesthetics, analgesics and antipruritic agents such as zinc pyrithione.

The compounds of this invention may also be deliverable transdermally for systemic distribution. The transdermal compositions can take the form of creams, lotions and/or emulsions and be included in a transdermal patch of the matrix or reservoir type as are conventional in the art for this purpose.

The compounds of this invention may be administered by any conventional mode of administration by employing an anti-allergic, anti-inflammatory or antihyperproliferative effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 500 mg/kg of body weight per day may be administered. For example, when administered orally they exhibit antiallergy activity at dosages of from about 0.5 to about 200 mg/kg of body weight and preferably about 50 to about 100 mg/kg of body weight; when administered by inhalation, the compounds exhibit antiallergy activity at dosages of 0.1 to 5 mgs per puff, and one to four puffs may be taken every 4 hours.

The compounds of this invention can be administered by any conventional mode of administration, to obtain the anti-inflammatory activity by employing an anti-inflammatory effective amount of a compound of this invention. The compounds of this invention, as an anti-inflammatory agent, may be administered at doses of about 0.1 to about 500 mg/kg of body weight per day, and preferably about 5 to about 200 mg/kg per day. Preferably the total dosages are administered in 2 to 4 divided doses per day. For example, an oral dosage range of from about 5 mg/kg of body weight per day to about 50 mg/kg of body weight per day in divided doses taken at about 4 hour intervals may be used.

When administered for the treatment of hyperproliferative skin disease, the compounds of this invention may be administered topically, orally, rectally or parenterally, preferably topically. When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered orally, the compounds of RED OIL and GOLD OIL are effective for the treatment of hyperproliferative skin disease at daily doses ranging from about 0.1 mg/kg to about 500 mg/kg of body weight, preferably from about 5 mg/kg to about 100 mg/kg, which may be administered in divided doses. When administered rectally, the compounds of this invention may be administered in daily doses ranging from about 0.1 mg/kg to about 100 mg/kg.

As a result of the administration of a compound of this invention, a remission of the symptoms of the psoriatic patient, in most cases, can be expected. Thus, one affected by psoriasis can expect a decrease in scaling, erythema, size of the plaques, pruritus, and other symptoms associated with psoriasis. The dosage of medicament and the length of time required for successfully treating each individual psoriatic patient may vary, but those skilled in the art of medicine will be able to recognize these variations and adjust the course of therapy accordingly.

Lipoxygenase Systems

Arachidonic acid serves as the biological precursor for a family of physiologically active eicosanoids. These include products derived from the action of cyclooxygenase such as the class of prostaglandin-E and -F compounds, thromboxanes, and prostacyclin, and products derived from the action of lipoxygenase enzymes such as hydroxy- and hydroperoxyeicosatetraenoic acids and the leukotrienes.

These lipoxygenase products have been shown to be highly potent stercospecific inducers of polymorphonuclear leukocyte migration or chemotaxis, lysosomal enzyme release, and degranulation. Additionally, these products induce the contraction of smooth muscle such as vascular and pulmonary tissue, and induce the generation of additional inflammogens such as thromboxanes $A_2$ and prostacyclin. Lipoxygenase products also interact with vasodilator prostanoids and other mediators, leading to the enhancement or amplification of the inflammatory response.

Leukotrienes and the hydroxy and hydroperoxyeicosatetraenoic acids play a major role in the pathogenesis of many disease conditions. These compounds have been found in synovial fluid of rheumatoid joints, in involved skin of psoriatic patients, in inflamed colonic tissue, and at elevated levels in ischemic myocardial tissue. They are also mediators of allergic and asthmatic conditions.

A role for 5-HETE in stimulating growth of a number of different types of tumors has recently been demonstrated in a number of publications. For example, the addition of arachidonic acid to cultured human prostate cancer cells resulted in a significant increase in cell growth and an increased biosynthesis of 5-hydroxycicosatetraenoic acid (5-HETE) (Ohosh and Myers, 1997). This increased growth was blocked by the 5-lipoxygenase (5-LO) inhibitors AA681 and MK886, but not by the 12-LO inhibitors, baicalein and N-benzyl-N-hydroxy-5-phenylpentanamide (BHPP) nor by cyclooxygenase (COX) inhibitors. Furthermore, the addition of 5-HETE, but not other products of the 5-LO pathway such as leukotriene $B_4$, to cells not only stimulated cell growth but also reversed the effect of MK886. Similar findings have also been observed in other types of cancer cells both in vitro and in vivo. For example, in human breast cancer (HS578T) cell line, the LO inhibitors nordihydroguaiarctic acid (NDGA) and esculetin inhibited cell growth, but the COX inhibitor piroxicam had no effect (Hofmanova et al., 1996). In the murine adenocarcinoma cell line (MAX) and mice transplanted with MAC cells, 5-LO inhibitors BWA4C (an acetohydroxamicacid with die general formula R-CONHOH) and BWB70C (an acetohydroxamic acid derivative) inhibited tumor cell growth and 5-HETE production (Hussey and Tisdale, 1996). Furthermore, in in vivo studies in A/J mice with adenoma induced by urethane, administration of NDGA significantly decreased lung adenoma cell number (Moody et al., 1998) and in murine adenocarcinoma, BWA4C and BWB70C were also shown to decrease MAC26 and MAC 16 cell growth by effects on both 5- and 12-HETE production (Hussey and Tisdale. 1996).

12-HETE

Increasing evidence suggests that 12-HETE, generated by platelets and tumor cells is a crucial molecule in promoting tumor metastasis. It enhances tumor cell induced platelet aggregation and tumor cell adhesion to subendothelial matrix by increasing expression of surface integrins, induces endothelial cell retraction, and increases tumor cell motility, all of which are important steps in tumor cell metastasis (Honn et al., 1994). In vitro studies have shown that the 12-LO inhibitor BHPP abolishes the above effects of both endogenously and exogenously added 12-HETE (Honn et al., 1992; Chen at al., 1994). It has also been demonstrated that 12-HETE production is a good indicator of tumor cell metastatic potential. For example, 12-HETE mRNA levels are elevated in prostate cancer cells compared with normal cells, and this increase in mRNA level correlates with advanced stages and poor differentiation of cancer cells (Gao et al., 1995). In further studies, it has been shown that rat Walker carcinoma (W256) and mouse melanoma (B16a) cells metabolize arachidonic acid (AA) to 12-HETE and 5-HETE and, that in experimental metastasis, utilization of BHPP decreases colony formation in the lung (Chen et al., 1994; Liu et al., 1994).

Compounds, pharmaceutical and nutraceutical compositions in accordance with the present invention inhibit lipoxygenase or the biosynthesis or biochemical action of leukotrienes and, therefore, are useful in the treatment or amelioration of a number of diseases whose pathogenesis involves the production of the leukotrienes and other lipoxygenase-derived products such as 5-HETE and 12-HETE, and leukotriene $B_4$ ($LTB_4$). These lipoxygenase inhibitors aid in the prevention of tissue damage and inflammation which result from infiltration of leukocytes, release of tissue-digesting lysosomal enzymes, and changes in the permeability and contractile state of smooth muscle tissue.

Specific conditions in which such lipoxygenase-inhibiting or leukotriene-antagonizing compounds and pharmaceutical compositions in accordance with the present invention are useful include allergy: asthma; arthritis; skin disorders including psoriasis and acne; inflammation; inflammatory bowel diseases, pain, and cardiovascular disorders including myocardial ischemia and infarction, angina, arrhythmias, stroke, atopic dermatitis, atherosclerosis and cancers of various etiologies including cancers of the prostate, lung, skin and digestive tract.

Angiogenesis Inhibition by RED OTT, and GOLD OIL of the Present Invention

There has been much scientific interest in the search for new inhibitors of angiogenesis with the view that this inhibition of new blood vessels will limit the growth of neoplastic tumors which depend on new vascular growth. As a normal cell develops into a solid tumor, it undergoes a series of changes. At the physiological level, growth is enhanced, immunity evaded, and neovascularization induced. Neovascularization or angiogenesis appears to be a prerequisite for tumor growth. Experimental solid tumors are unable to grow beyond a few millimeters in thickness without a blood supply. Most natural solid tumors elaborate angiogenic factors that attract the new blood vessels on which they depend. Thus, there has been a continuing research effort directed toward the questions of what it is that may prevent rampant capillary proliferation and what maintains the quiescent state of the capillary endothelial cells of normal tissues.

An additional object of the present invention is to provide a composition of matter and a method of inhibiting angiogenesis in a warm-blooded animal in need of such treatment, which comprises administering to said warm-blooded animal a therapeutically effective amount of a composition comprising the isolated RED OIL or GOLD OIL, or LIGHT or HEAVY Phases from molecular distillation processes as described in the following sections.

Carotenoids from Sea Cucumber Tissues

Carotenoids from sea cucumbers have been mentioned in various scientific journal articles, to wit: Matsuno et al. (1995) reported the occurrence of astaxanthin as the major carotenoid in the gonads of the sea cucumbers *Holothuria leucospilota* and *Stichopus japonicus*, and beta carotene, echinenone, canthaxanthin and zeaxanthin were identified from the gonad of *H. leucospilota* and *S. japonicus*. On the other hand, astaxanthin and the esters, canthaxanthin, phoenicoxanthin and echinenone, were isolated by Bullock and Dawson (1970) from the red body wall of *Psolus fabrichii*. Tsushima et al. (1996) reported on the novel marine di-Z carotenoids, cucumariaxanthins A, B and C from the sea cucumber *Cucumaria japonica*. Findlay et al. (1983a) reported on canthaxanthin from tile species, *Cucumaria frondosa*. None of these reports provide any means whereby to utilize such carotenoids for any aquaculture or medical or health food industry applications, and none provide methods to concentrate such pigmented lipid fractions.

U.S. Pat. No. 4,692,280 by Spinelli, Stout and Nilsson describes a method for obtaining purified fish oils (after initial extraction from fish tissues) using supercritical carbon dioxide, and is incorporated herein by reference for the purpose of describing said methods. This patent does not disclose a means of obtaining sea cucumber lipid fraction purification through the supercritical purification methodologies set forth in the patent.

Thus, there is no prior art for the efficient and large scale removal of lipid fractions, and none directed at obtaining usable carotenoid or non-carotenoid lipid fractions of sea cucumber tissue.

It is an object of the present invention to provide a means to recover usable pigmented lipid fractions and pigment-free lipid fractions from the intestinal gut material and/or body walls from sea cucumbers, especially from the species *Cucumaria frondosa*. It is a further object of the present invention to disclose a composition of matter which is the pigmented lipid fraction and a de-pigmented lipid fraction resulting from such means of recovery. The resultant pigmented lipid fraction, obtained by an acetone or alcohol solvent extraction with commercial extraction equipment, such as the Crown 2 Extractor (Crown Iron Works, Chicago, Ill.), as is used in the soy-bean oil extraction arts, provides a pigmented material rich in canthaxanthin and astaxanthin at approximately 4,500 parts per million, and is useful in the aquaculture industry as a feed ingredient. After lipid extraction, the dry, de-lipidized tissue can be utilized as a high-protein meal or hydrolysate with surprising levels of essential amino acids.

SUMMARY OF THE INVENTION

The present invention sets forth methods and compositions of matter for the industrial extraction of novel pigmented and non-pigmented lipid compounds obtainable from sea cucumber gut or body-wall tissue in wet or dry raw material conditions. The compounds of the present invention are able to be used as pigmenting additives in aquatic diets or as medically therapeutic agents in mammals, and are produced by molecular distillation techniques, solvent extraction techniques on industrial scales, column chromatography techniques and through preparative high pressure liquid chromatography techniques that are described herein.

The compounds of this invention demonstrate anti-inflammatory activity made apparent by the low percent increase in ear weight in murine models of inflammation and when applied topically, and by the results of inhibition of adjuvant induced inflammation in tile hind paws of rats, as well as from anecdotal reports of subjective benefit from humans.

The compounds of this invention, the RED OIL and GOLD OIL and the molecular distillation fractions thereof are used to treat allergies in mammals (e.g. humans or dogs) and a preferred use is for treating allergic chronic inflammations of the dermis of such mammals, and with appropriate transdermal carrier compounds, as inhibitors of arthritic inflammatory conditions wherein the oils of the present invention are carried transdermally to the sites of lipoxygenase all activation locally. An additional preferred use is for treating allergic chronic obstructive lung disease. Chronic obstructive lung disease as used herein means disease conditions in which the passage of air into and out of the lungs is obstructed or diminished such as is the case in asthma, allergic or seasonal rhinitis, and/or bronchitis and the like. Treatment of psoriasis, acne, arthritis, or cancer can be accomplished by use of the compounds of the present invention as topical compounds as well as by oral administration.

Therefore, an additional object of the present invention pertains to the immunosuppressive use of the RED OIL and GOLD OIL isolated from sea cucumber tissues, and various derivatives and analogs of these compounds. These compounds can be used to reduce, suppress, inhibit, or prevent unwanted immune responses. Advantageously, this immunosuppression can be achieved without cytotoxicity. Therefore, these compounds are useful for treatments of humans or animals requiring immunosuppression. Examples of such situations include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents. The subject invention further pertains to pharmaceutical compositions containing these compounds.

As pigment additives, the various pigmented oils can be added to fish or shrimp feeds at various inclusion rates depending on the carotenoid content of the oil or the desire for certain intensities of color in particular aquatic species being fed the pigmented diet.

DETAILED DESCRIPTION OF THE INVENTION

METHODS OF PREPARING USEFUL FRACTIONS OF SEA CUCUMBER

Figure 1:
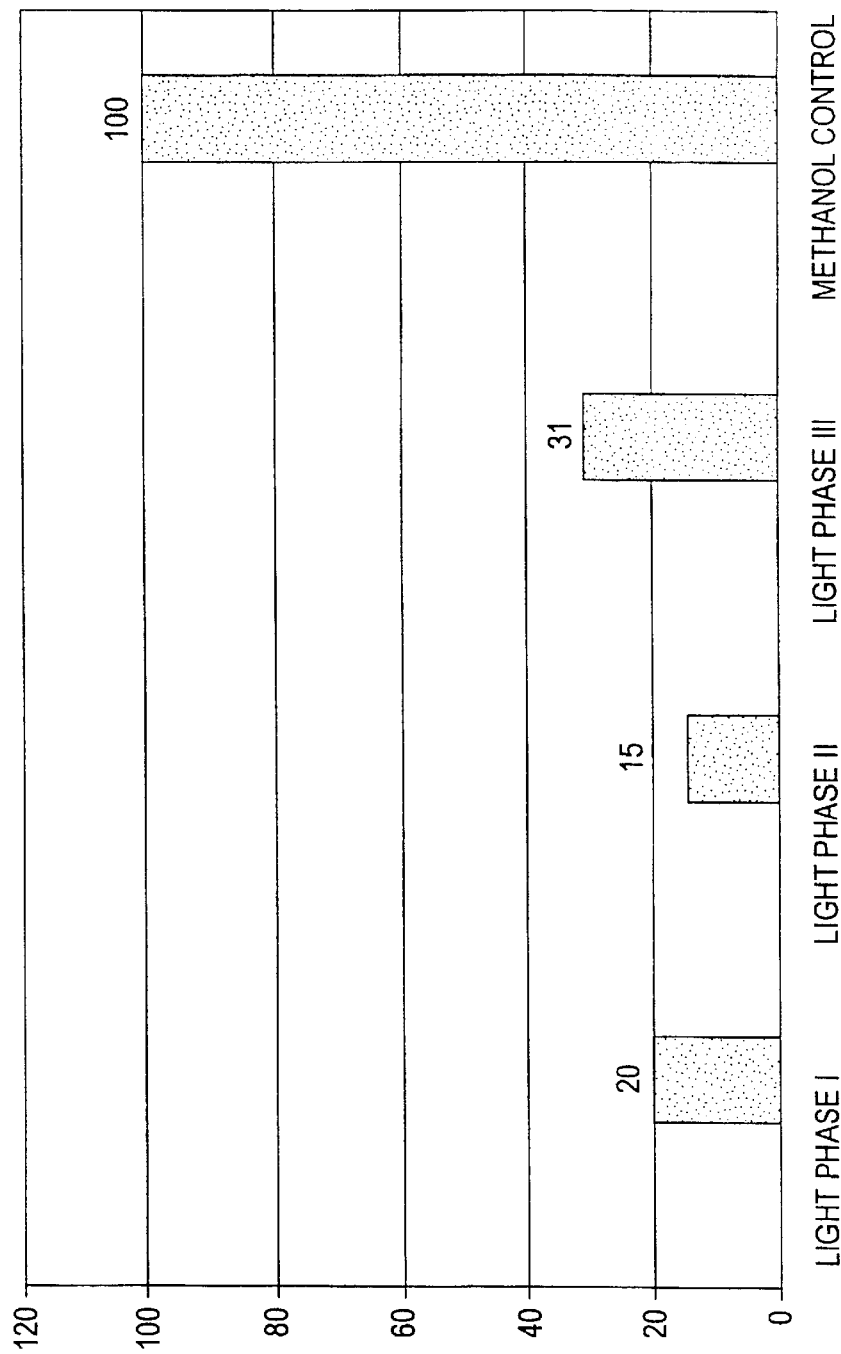
FIG. 1 shows the effect of GOLD OIL LIGHT PHASES on the synthesis of $LTB_4$ compared to control.

Various fractions of sea cucumber are isolated and used either therapeutically or as part of aquatic feed. In brief, one method of preparing these fractions involves extracting dried sea cucumber gut or body wall with a solvent to produce a pigmented oil called RED OIL. The pigments can be removed from RED OIL to yield a more-or-less depigmented oil called GOLD OIL as well a second fraction which is a red pigmented lipid concentrate. The RED OIL and the GOLD OIL can each be distilled to yield various fractions including what are called LIGHT PHASES and HEAVY PHASES. Another approach is to use wet sea cucumber tissue rather than dried tissue. When this is done with acetone or alcohol, the first solvent extraction yields a product referred to as RED GREASE. A second method of making GOLD OIL is also set out. This alternate method involves a second solvent extraction of sea cucumber tissue that is dried by any suitable means after the first extraction has removed all or most of the red color. Finally, another fraction of sea cucumber is obtained by taking the sea cucumber tissue which has been delipidized and treating it to produce a protein-rich hydrolysate. This hydrolysate is useful as a food supplement or can be incorporated into a variety of foodstuffs. Methods of making and using each of the fractions are set out below. The methods below set out more than a single method for making each of the various products of the invention, such as the RED OIL and the GOLD OIL. Although slightly different methods are set out, the methods produce essentially equivalent products and the name of the product is meant to encompass a product regardless of which method set out in this disclosure or other method which yields an essentially equivalent product with similar activities or uses is used to prepare the product.

A Method of Preparing Useful Fractions of Sea Cucumber

The intestinal mass from 460 kilograms of sea cucumber, *Cucumaria frondosa*, was collected from the processing wastes of a sea cucumber industry. The intestinal mass (352 pounds) was dried in a conventional low heat seafood dryer (Southwind, Nova Scotia, Canada) on screen racks for 3 days resulting in 105 pounds of dried material. The dried intestinal mass was subsequently extracted by hexane as is known in the soybean oil arts with conventional methods (Crown Model 2 Extractor, Crown Iron Works, Chicago, Ill.) to produce approximately 42 pounds of red lipid material referred to as RED OIL. The lipid material was then 'degummed' by the addition of 1% water to the oil, allowed to hydrate for 30 minutes and then centrifuged at 8000 rpm at 150° F. The red degummed lipid material was subsequently pretreated with 0.5% silica gel, heated to 180° F. and then filtered out using 6 micron filter paper. The removal of the pigment was conducted by adding 5% bleaching clay to the pretreated oil. The oil was heated to 220° F. for 20 minutes at 28 inches Hg of vacuum. The resulting oil (34 pounds) was light yellow color and most of the pigment was adsorbed in the bleaching clay. The intestinal lipid, free of pigments, is designated "GOLD OIL" and is one of the lipid fractions further assayed for inhibition of lipoxygenase activity and anti-inflammatory activity.

The resulting clay was then extracted with acetone 1:2 (w:w) clay to solvent ratio and washed twice. The resulting solution was then desolventized in a Luwa evaporator at 90° C. and 29 inches Hg vacuum and 8 pounds of red lipid fraction concentrate was recovered.

An alternate method of preparing GOLD OIL is to pass RED OIL through a column of silicic acid equilibrated with chloroform and wash the column with chloroform. GOLD OIL elutes with the chloroform wash. A concentrated RED OIL can then be eluted from the column by passing a chloroform:methanol (preferably 60%:40%) mixture through the column. This results in about 70% of the original material loaded onto the column being recovered as GOLD OIL and 30% being recovered as concentrated RED OIL.

Figure 2:
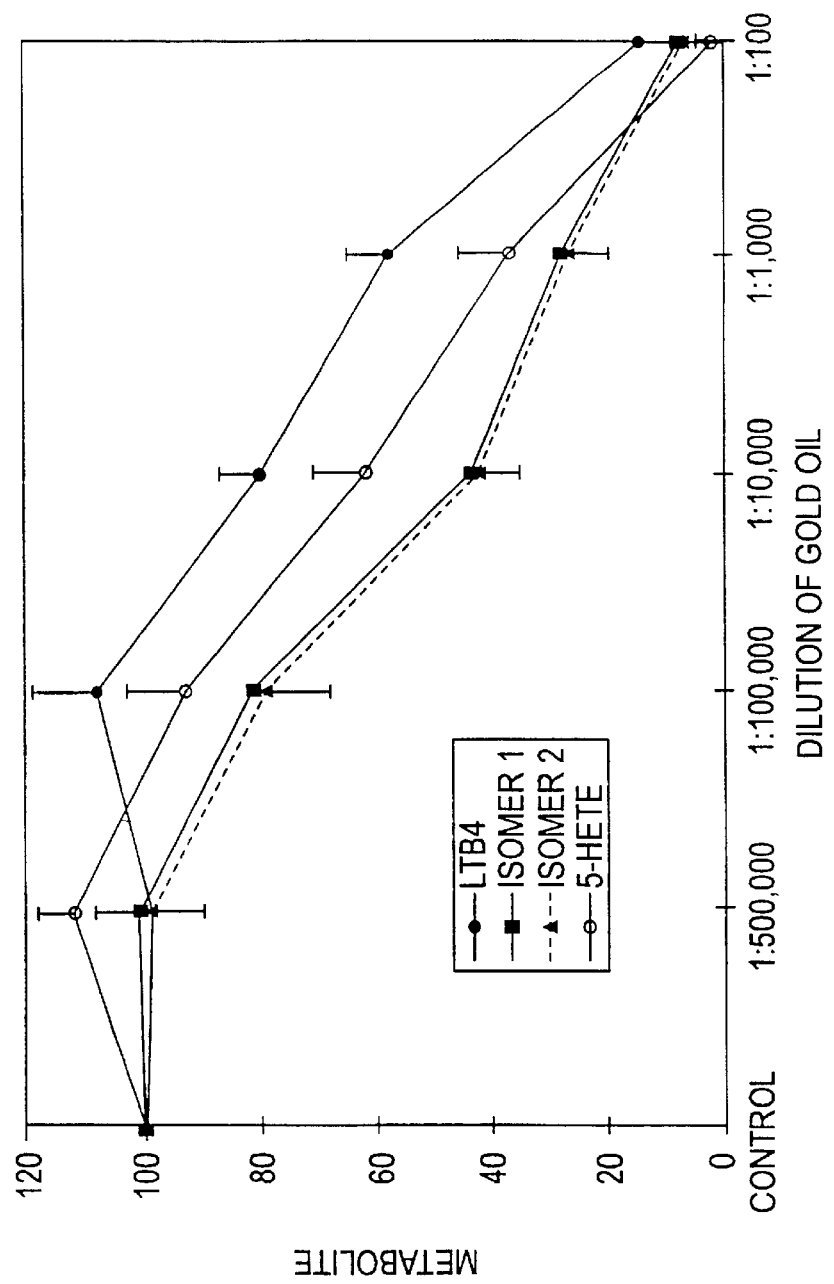
FIG. 2 shows the inhibition of neutrophil 5-lipoxygenase metabolite synthesis by dilutions of GOLD OIL.
Figure 3:
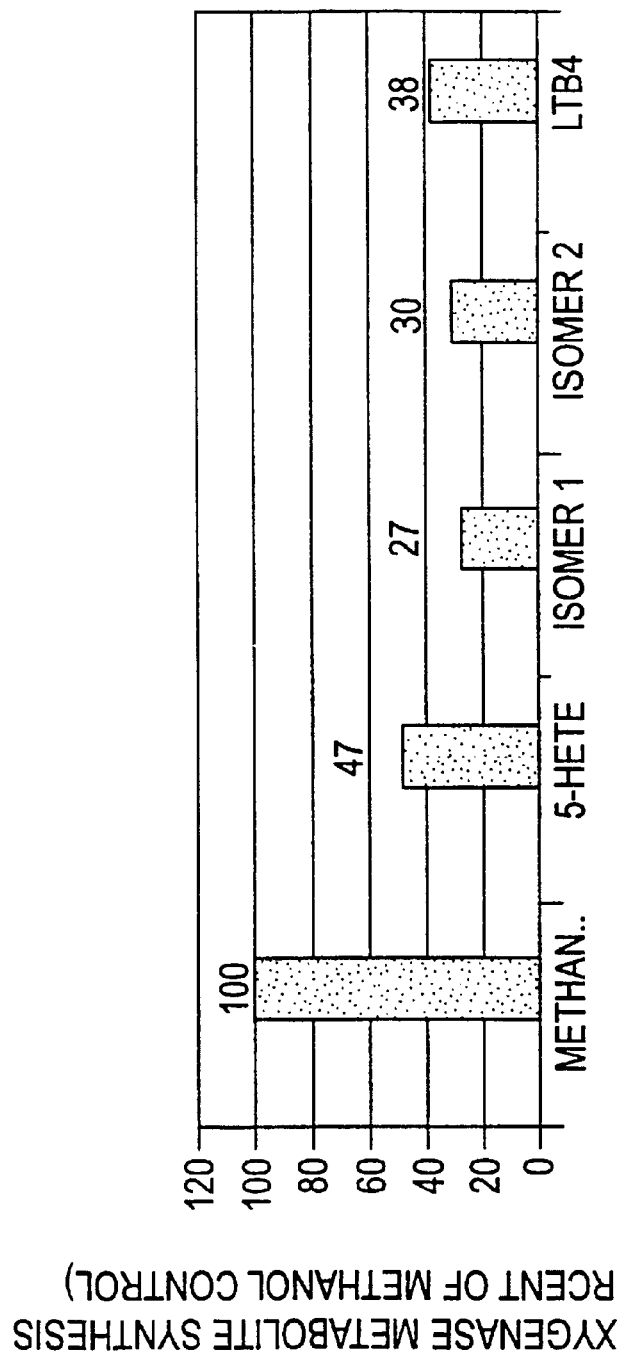
FIG. 3 shows the effect of RED OIL at a dilution of 1:10,000 on neutrophil 5-lipoxygenase metabolite synthesis.
Figure 4:
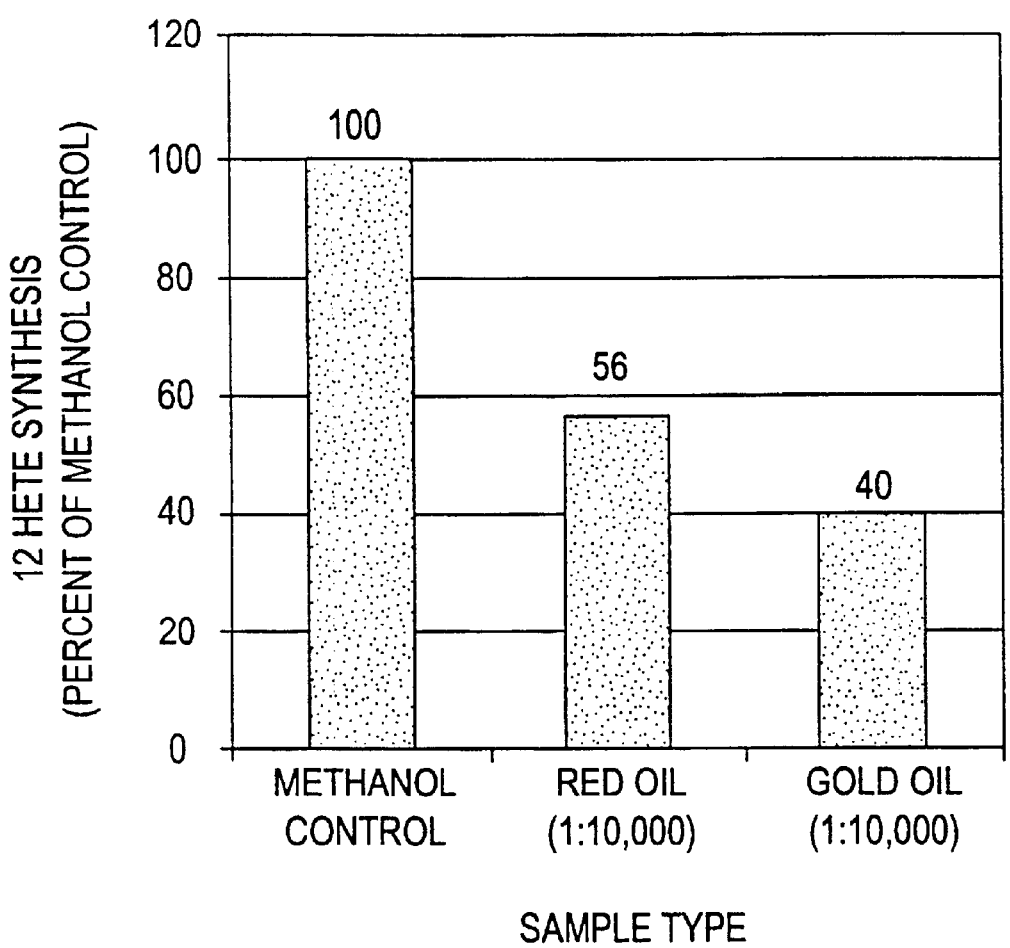
FIG. 4 shows the effect of RED OIL and GOLD OIL on 12-HETE synthesis compared to methanol control.
Figure 9:
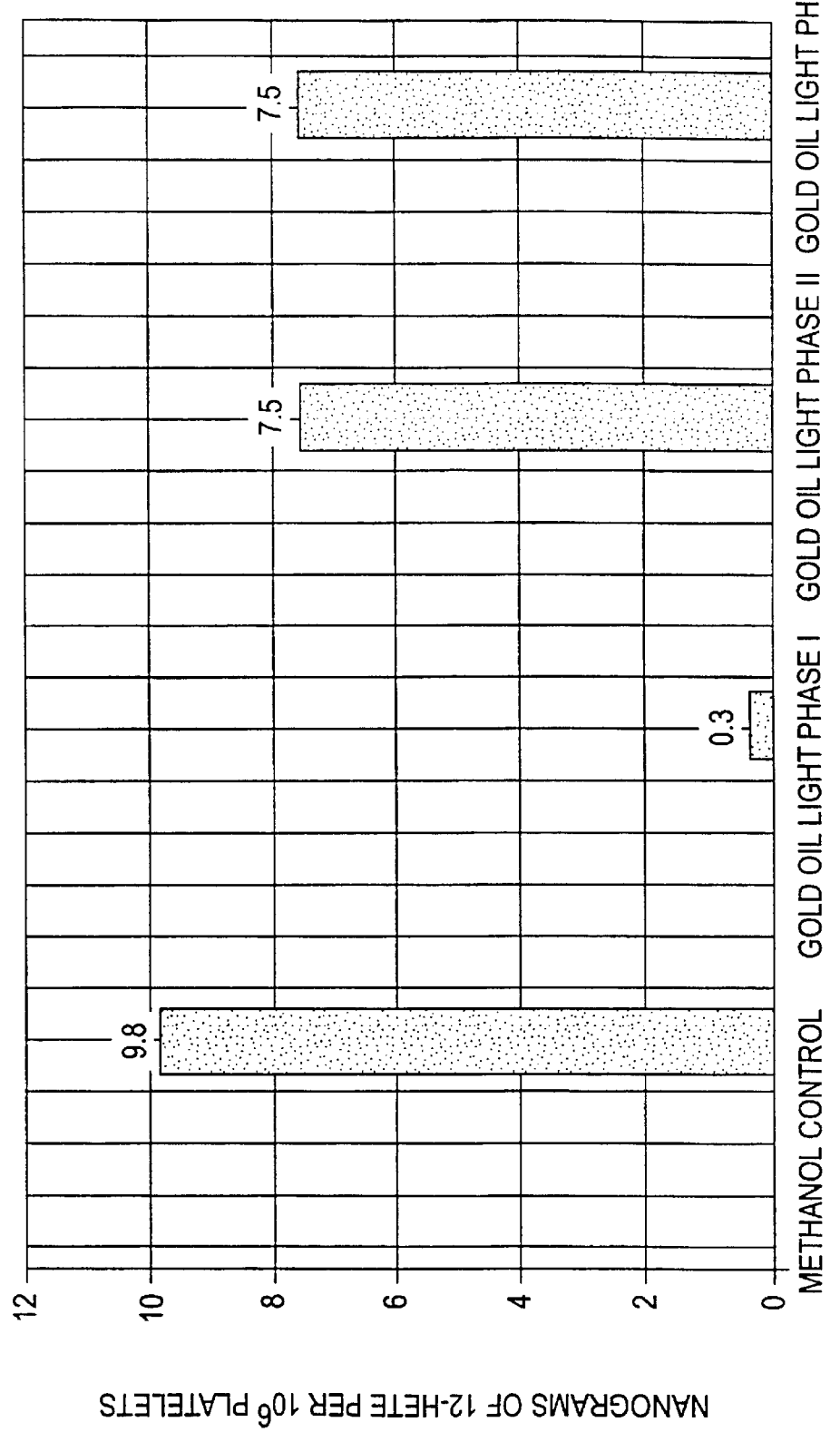
FIG. 9 shows the effect of the GOLD OIL LIGHT PHASES on 12-HETE synthesis compared to methanol control.

The pigment-free GOLD OIL and the pigmented RED OIL were both subjected to molecular distillation in order to separate evaporative fractions. Three passes were made through a molecular still at 200° C. and 0.005 torr. Three fractions in every pass were recovered. The light phase (LIGHT PHASE I) was collected with a condenser temperature of about 30° C. and retained. The volatile fraction was collected in an alcohol/dry ice trap and discarded. The heavy phase (HEAVY PHASE I) was that portion that eluted at the bottom of the still, un-evaporated by the process. HEAVY PHASE I was subsequently reintroduced to the molecular still and produced LIGHT PHASE II and HEAVY PHASE II. The HEAVY PHASE II which eluted at the bottom of the still was then reintroduced to the still and produced LIGHT PHASE III and HEAVY PHASE III. In total, these techniques provided LIGHT PHASES I, II and III; HEAVY PHASES I, II and III; and additional volatiles which were discarded. Light Phases were subsequently assayed for their activity in inhibiting lipoxygenase pathways. FIG. 1 depicts the inhibition of the 5-lipoxygenase activity of the Light Phases. FIG. 2 depicts the inhibitory 5-lipoxygenase activity of un-distilled GOLD OIL. FIG. 3 depicts the 5-lipoxygenase inhibiting activity of RED OIL prior to de-pigmenting. FIG. 4 depicts the effect of GOLD OIL and RED OIL on the activity of the 12-lipoxygenase pathway and the generation of 12-HETE. FIG. 9 depicts the effect of GOLD OIL LIGHT PHASES at a dilution of 1:1000 on 12-HETE synthesis compared to methanolic control.

A Second Method of Preparing Useful Fractions

The objects of the present invention which include the use of the subject oil fractions from sea cucumber gut or body-wall tissue as pigment-providing compounds for the pigmenting of fish or shrimp are accomplished by embodying a process, the steps of which include, in combination:

a. Separating gut material from the processed sea cucumber by hand or machine. Hand separation involves cutting the animal with a knife and physically removing the intestines. Machine cutting involves any mechanized embodiment wherein automated cutting tools are able to cut open the animal whereby the intestines are available for removal.

b. The proteinaceous lipid gut material is pretreated after separation from the animal with sufficient acid to lower the pH of the material to within a range of from about 4 to about 5.5 preferably about 4.3 to about 4.7 to suppress microbial degradation, demineralize the mass and improve overall red carotenoid pigment recovery during the subsequent extraction with solvent or combinations of solvents.

c. In one method of processing, the proteinaceous lipid gut material is mixed with acetone, alcohol or similar solvent in 3:1 (v:v) solvent to material ratio and then agitated for 24 hours or until sufficient pigment has released from the gut material to the solvent.

d. The acetone or other solvent is decanted off of the remaining gut material and the gut material is washed subsequently four or more times with clean solvent to remove remaining carotenoid-bearing lipids.

e. The remaining gut material is centrifuged to purge remaining solvent, or heated in a closed vessel and the solvent reclaimed by methods using a desolventizer as known to those in the arts.

f. The pigment bearing acetone or solvent is pumped to a 'wiped-film' evaporator as is known in the oil chemist's arts and the pigment is retained and sequestered and the solvent is reclaimed.

g. The resultant lipid pigment fraction is a mixed carotenoid-bearing lipid material containing canthaxanthin and astaxanthin, and is referred to herein as "RED GREASE". The major carotenoid is canthaxanthin in the example of *Cucumaria frondosa*.

h. The resultant pigmented lipid fraction can be stabilized with known anti-oxidants as are known in the arts.

i. The remaining gut material is then dried and extracted with hexane, butane, supercritical carbon dioxide, or similar solvent to remove a golden oil essentially free of pigments. This golden oil, which is essentially free of most carotenoids is referred to as GOLD OIL. The resultant remaining dry proteinaceous material, free of lipids, is high in protein and polysaccharides and is suitable for inclusion into animal or human food excipients where essential amino acids are needed. The proteinaceous de-pigmented meal is unique in the marine fish-meal industry inasmuch as it is de-pigmented, de-lipidized, can be made water soluble by methods set forth herein, is high in usable protein and essential amino acids, and is essentially free of odoriferous contaminants. It is easily manufactured into powder or hydrolysate by methods known to those skilled in the hydrolysate arts and which are herein described.

In another embodying process of the present invention, the separated sea cucumber guts are dried after being acidified as described in the previous method. The gut material can also be heated in water at ranges between 150° F. and boiling, for various lengths of time between 10 minutes and 30 minutes, prior to being acidified without adversely affecting the general process of the invention. The drying process can be low heat (60–80° F.) or higher heat (150–200° F.) without affecting the target lipid fractions or carotenoids. This embodying process which includes drying the gut or tissue material is further accomplished by steps which include, in combination:

a. Subjecting the dried gutmaterial which has a moisture content of less than approximately 10% to a standard "oil-recovery procedure" with hexane or other suitable solvent known to those skilled in the arts, wherein the dry gut or tissue material is mixed at 1:1 ratio at 130° F. for 5 minutes and then drained. The extracted product is then washed three times with fresh solvent. The solution containing the carotenoid is desolventized in a wiped film evaporator (Luwa and Pope) at 95° C. and 28 inches Hg vacuum.

b. Sequestering the solvent/lipid phase into containers designed for such use and freeing said solvent from carotenoid-oil/solvent phase by standard "steam stripping" or by "wiped film" oil technology.

c. Treating such oil phase with anti-oxidants which are known to those skilled in the arts such as 6-ethoxy-1, 2-dihydro-2,2,4-trimethylquinoline (Ethoxyquin, Monsanto) at between 300 to 600 parts per million or vitamin E at approximately 1 percent.

d. Subjecting the red pigmented oil thus obtained to a degumming process by the addition of 1% water to the oil then allowing to hydrate for 30 minutes and then centrifuging at 8000 rpm at 150° F. This oil is referred to as RED OIL.

e. Recovering the concentrated pigment in the following manner:

The degummed oil is first pretreated with 0.5% silica gel (Trysil 600, Grace Co.). heated to 180° F. and then filtered out using 6 micron filter paper. The recovery of the color is conducted by adding percent bleaching (activated) clay (Englehard 105) to the pretreated oil and the oil is then heated to 220° F. for 20 minutes at 28 inches Hg of vacuum. The resulting oil is light yellow color and most of the pigment is adsorbed in the bleaching clay. This oil is referred to as GOLD OIL. The resulting clay is then extracted with acetone 1:2 (w:w) clay to solvent ratio and washed twice. The resulting solution is then desolventized in an evaporator (Rotovap) at 90° C. and 29 inches Hg vacuum.

f. Determining the carotenoid content of extracted concentrate by standard HPLC methods known to those skilled in the arts. Concentrated pigment extracted by this present invention is suitable for inclusion in aquatic diets and contains parts per million of carotenoids canthaxanthin at between 2,000 and 5,000, depending on the carotenoid content of the original material.

g. Stabilizing de-pigmented lipid from the carotenoid extraction procedure (GOLD OIL) by the addition of vitamin E or other suitable antioxidants known to those in the arts, at between 1 and 5% by weight.

h. Encapsulating de-pigmented lipid fraction (GOLD OIL) or the pigmented oil (RED OIL) obtained from the carotenoid bearing oil extraction procedure of sea cucumber intestinal mass in "soft-gel" capsules of 500 to 1000 milligrams, or packaging into suitable containers for oral and topical administration to mammals. Topical administration products can be obtained by any combination of emollients combined with the non-pigmented lipid fraction, depending on desired effect in a specific or general condition.

i. Incorporating said pigmented lipid fraction, depending upon parts per million of carotenoid, into aquatic diets at a percentage of such food sufficient to produce carotenoid deposition into flesh or skin.

Further Methods of Preparing Useful Fractions

It is a further object of the present invention to disclose a composition of matter comprising the sea cucumber gut lipid fraction essentially free of carotenoids. It is relatively odorless; contains significant amounts of the omega-3 fatty acid, EPA (eicosapentanoic acid); and contains vitamin E.

Figure 5:
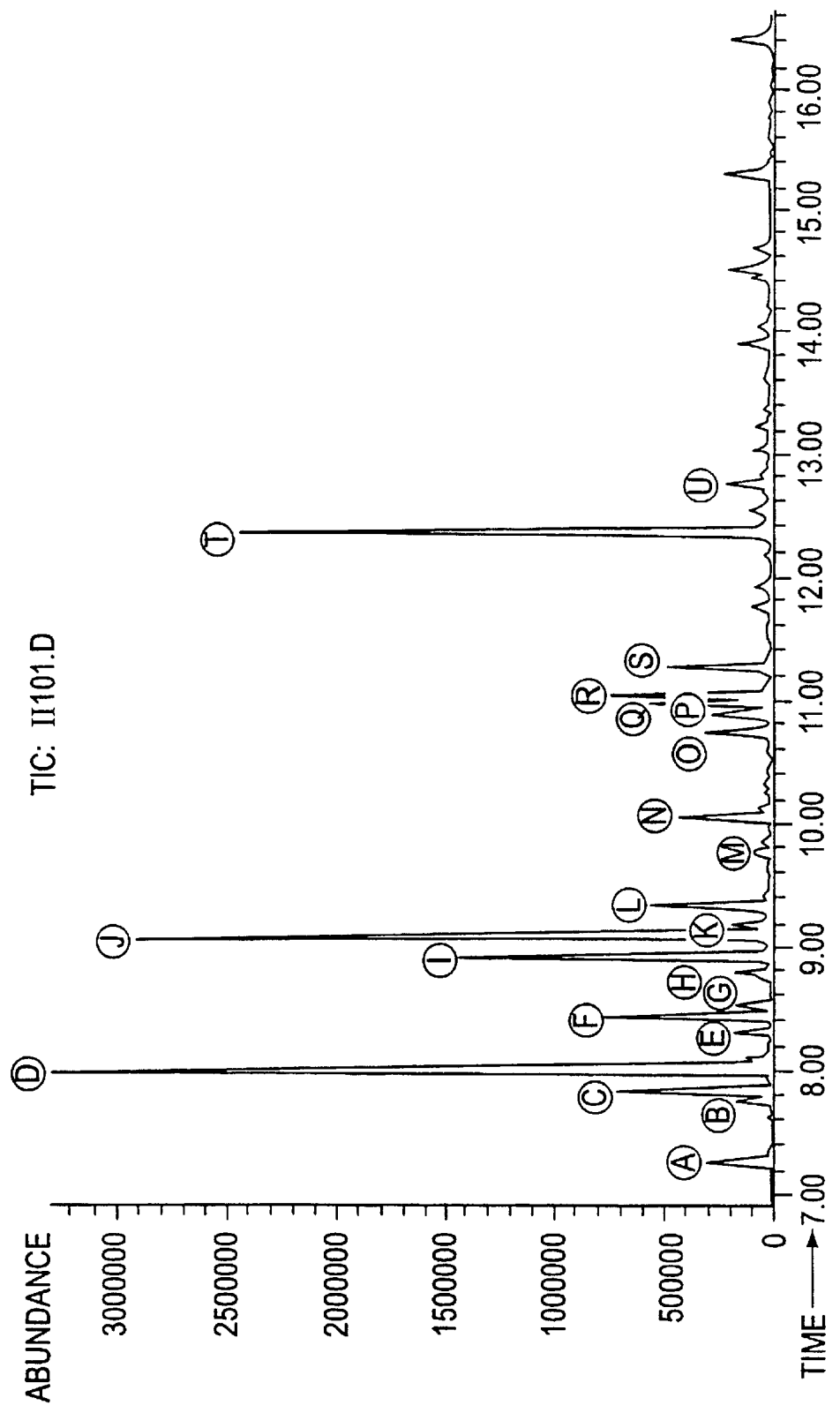
FIG. 5 shows a gas chromatograph of GOLD OIL.

Gas chromatography/mass spectrometry was performed on the de-pigmented lipid fraction. The gas chromatograph data appears in FIG. 5. FIG. 5 is the spectrum of the de-pigmented lipid fraction after extraction of carotenoids by the means of activated clay transference, and was performed with a Hewlett-Packard Model 5890 Gas Chromatograph and a 5971 Mass Selective Detector (Mass Spectrometer). The column used in analysis was an HP Ultra-1 Capillary GC column 25 mm long. The de-pigmented lipid fraction was first saponified to free fatty acids using sodium methoxide, as is standard in the lipid analytical arts, and then acidified, and then converted to methyl esters. Subsequent synthetic methyl esters thus produced were compared to standard profiles of fatty acids from known reference libraries. Table 1 compares the percentage of match of the fatty acids from the sea cucumber de-pigmented lipid fractions with known fatty acid profiles.

TABLE 1

| Peak | Compound from Library | % Match |
|---|---|---|
| A | tetradecanoic acid, methyl ester | 97 |
| B | 2-naphthol, 8-amino | 64 |
| C | pentanamide | 49 |
| D | pentadecanoic acid, methyl ester | 91 |
| E | pentadecanoic acid, methyl ester | 98 |
| F | hexadecanoic acid, methyl ester | 43 |
| G | pentadecanoic acid, 4-methyl-, methyl ester | 64 |
| H | hexadecanoic acid, methyl ester | 41 |
| I | hexadecanoic acid, methyl ester | 87 |
| J | 7-hexadecanoic acid, methyl ester | 99 |
| K | 9-hexadecanoic acid, methyl ester | 98 |
| L | pentadecanoic acid, 14-methyl-, methyl ester | 93 |
| M | hexadecanoic acid, 14-methyl-, methyl ester | 93 |
| N | hexadecanoic acid, 15-methyl-, methyl ester | 78 |
| O | 1,2,8-dodecatriene, (E,E,E)- | 94 |
| P | 10,13-octadecadienoic acid, methyl ester | 98 |
| Q | 9-octadecenoic acid (Z)-, methyl ester | 99 |
| R | 7-octadecenoic acid, methyl ester | 99 |
| S | octadecenoic acid, methyl ester | 98 |
| T | methyl eicosa-5,8,11,14,17-pentaenoate | 80 |
| U | 7-hexadecanoic acid, methyl ester (Z) | 91 |

It is a further object of the present invention to disclose a composition of matter comprising the sea cucumber gut material which has been de-lipidized through the methods herein described. This material is unique inasmuch as it is essentially free of odor, high in protein, and is easily made into useable powder. The two examples which immediately follow are illustrative of typical runs selected from a number of runs made using the differing techniques and solvents. Body wall tissues contain less lipid than the intestinal gut masses and are extracted by the same methods described for gut materials of sea cucumbers. The lipid fraction content of body wall tissues is much less, however, than gut material, or about 1 to 2% of total dry weight of body-wall tissue.

Figure 6:
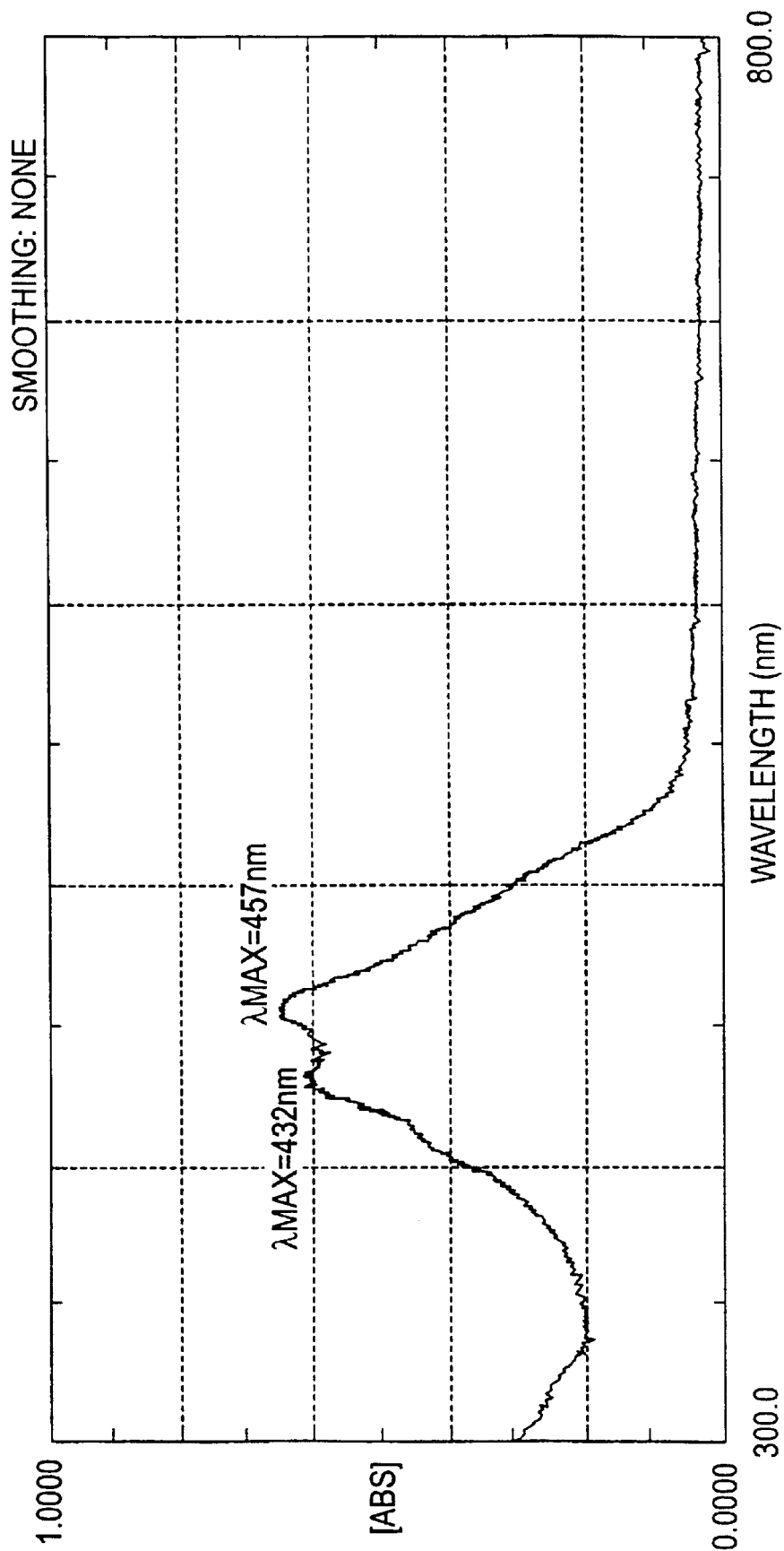
FIG. 6 shows an absorption spectrum of RED OIL.

The pigmented lipid fraction of sea cucumbers, referred to as RED GREASE, is incorporated into aquatic diets at a percentage of such food (depending upon parts per million of carotenoids) sufficient to produce carotenoid deposition into flesh or skin. It is an object of the present invention to disclose a composition of matter comprising a carotenoid lipid fraction obtainable from sea cucumber gut or body tissue which contains varying percentages and parts per million, depending on environmental factors, of astaxanthin and canthaxanthin. One of the carotenoid lipid fractions so disclosed as RED GREASE was determined to contain 4,706.52 parts per million of canthaxanthin by spectrophotometric analysis. The absorption spectrum is attached hereto as FIG. 6. FIG. 6 shows an absorption spectrum which was obtained from a Beckman DU-800 chromatograph of the acetone extracted carotenoid lipid fraction of fresh sea cucumber gut material having a calculated ppm of 4,706.52 carotenoid content. Twenty three milligrams of acetone extracted carotenoid lipid fraction was diluted with 10 mL of petroleum ether with the carotenoid material having an extinction coefficient of E=2400 and read at 467 nm for canthaxanthin.

Fresh sea cucumber gut material as well as body tissues can be a source material of lipid compounds and can be extracted with hot edible oil as per the method of Meyers and Chen (1982). U.S. Pat. No. 4,505,963 (which is incorporated herein by reference), also of Meyers and Chen, discloses an industrial means whereby crawfish carotenoid pigments are extracted from processing waste utilizing hot oil. Although the applicability of this industrial method differs from a hot oil method possible using fresh sea cucumber gut material as a primary resource, the process is essentially the same inasmuch as both processes rely on the migration of carotenoid bearing lipids into the hot edible oil. Fresh gut material of *Cucumaria frondosa* (1 kg) was placed into a vessel of 5 kilograms soybean oil heated to 170° F. and allowed to stand for 20 minutes. The tissue was removed by filtration through a 200 mesh stainless steel screen and a common 'coffee filter' paper and excess oil was lightly expressed back into the cooking vessel. A subsequent 1 kilogram of gut material was placed into the vessel and the procedure was repeated with new batches of gut material. After 5 new batches of gut material processed in the above manner, the oil in the cooking vessel had turned dark red from the migration of gut lipids to the oil mixture. In one example of this procedure, starting volumes of 5 kilograms of soybean oil were produced in which 5 kilograms of wet gut material had been subsequently retained and then removed after approximately 20 minutes. Total carotenoid percentage in one such processed sample of the remaining oil was determined to be 540 parts per million by standard methods.

Production of De-lipidized Protein-rich Hydrolysate

Three hundred grams of sea cucumber gut tissue material was obtained as described herein, dried and de-lipidized through hexane extraction as is known to those skilled in the soybean oil arts. The resultant sea cucumber meal was desolventized by heat and air-flow and the resultant meal was collected. The meal was further put into solution with one liter of distilled water. Using concentrated sodium hydroxide, the pH was raised to 12, and this solution was stirred for thirty minutes. At the end of the thirty minutes, the pH was adjusted down to pH 8.5 using HCl. As soon as this pH was achieved, the solution was heated to 80° C. for one minute. This solution was allowed to cool to 25° C. and then was centrifuged at 10,000 rpm for 20 minutes, and the solids were disposed of as waste and the supernatant was adjusted to a pH of 3.0. The proteins were precipitated out of the solution and were removed from solution by centrifuging and decanting. The proteins were then dissolved in a minimal amount of water and pH was adjusted to 7.2 and then this was dried using a freeze dryer. It was found that the liquid hydrolysate is suitable for conventional spray-drying as is known in tile arts. Extraction efficiencies of the preliminary experiments indicated a 73% efficiency from starting material. The protocol described above was found suitable for production lots in larger vessels with machinery that is common to the food science and protein hydrolysate industry. The dried hydrolysate thus obtained was determined to be water soluble, and the amino acid profile of this material is as follows:

| | |
|---|---|
| Tryptophan | 0.82% |
| Aspartic acid | 8.14 |
| Threonine | 3.01 |
| Serine | 2.62 |
| Glutamic acid | 8.67 |
| Proline | 2.67 |
| Glycine | 4.21 |
| Alanine | 4.39 |
| Cysteine | 0.21 |
| Valine | 4.31 |
| Methionine | 1.00 |
| Isoleucine | 4.03 |
| Leucine | 3.38 |
| Phenylalanine | 4.39 |
| Lysine | 5.31 |
| Histidine | 1.88 |
| Arginine | 5.93 |

The sea cucumber hydrolysate described above is in suitable form for inclusion as a protein or pre-digested amino acid compound in liquid drinks, encapsulated food supplements, salad dressings, gravies, milk substitutes for infant formulas, protein bars, cosmetics, soft-drinks, pasta, breads, and enteral alimentation formulas for persons for whom protein malnourishment contributes to their nutritional condition. It is not necessary to include, herein, the variations in which such dried or liquid amino-acid rich powders may be incorporated and in what percentages to foods, inasmuch as these types of formulations are known full well to those skilled in the food science arts.

METHODS OF USE OF SEA CUCUMBER FRACTIONS

Examples of Pigmented Lipid Inclusion in Aquatic Diets

A) One hundred pounds of fresh sea cucumber gut material was mixed with approximately fifty-five gallons of acetone and agitated at room temperature for three hours in a 300 gallon closed vessel. The acetone was drained from the mixture into a containment vessel and fresh acetone was washed over the gut material until little pigment color was obtained. The acetone was pumped through a wiped film evaporator (Pope Still) and the water included in the acetone mixture and the acetone were separated from the pigmented lipid fraction and re-claimed. The acetone was salvaged and the water phase was discarded.

The resulting lipid fraction (0.63 pounds) had a heavy grease consistency and 4,700 parts per million of the carotenoid canthaxanthin. The antioxidant, 6-ethoxy-1,2-dihydro- 2,2,4-trimethylquinoline (Ethoxyquin, Monsanto) was added to the lipid phase and mixed at 1% by weight.

The heavy lipid fraction containing carotenoid material (RED GREASE) was determined to contain 4,700 parts per million of canthaxanthin by HPLC analysis and was incorporated into standard ornamental fish feed which had had the commercial carotenoid material excluded in its manufacture. The fish feed was formulated by the manufacturer so that it ultimately contained 80 parts per million of the sea cucumber derived canthaxanthin. Clownfish were fed an experimental diet of this feed for two months and were judged by a panel of 5 judges giving an average number score of 8.5 (on a scale from 1 to 10, with "10" being a very acceptable color deposition), to have deposited acceptable color to their skin. (B) Sea cucumbers (1000) of the species *Cucumaria*

*frondosa* were eviscerated by hand and the gut material (352 pounds) was dried by low heat means at 70° F. for 4 days in a seafood dryer (Southwind, Nova Scotia). Prior to drying, propionic acid was added to the fresh, wet sea cucumber gut material at 7.2% by weight. The resultant dried material (105 pounds) contained 10% moisture and 41% lipids. The dry gut material was then subjected to hexane extraction of the lipid fraction as per industry standards in a 200 gallon closed vessel, essentially the same process used in the soybean oil industry, and a red lipid fraction (42 pounds) (hereinafter referred to as RED OIL) containing 924.5 parts per million carotenoid judged as canthaxanthin with 8.8% eicosapentanoic fatty acid was produced. This lipid fraction also contained 35 IU d-α-tocopherol per 100 grams. The red lipid fraction (RED OIL) was then degummed by the addition of 1% water to the oil then allowed to hydrate for 30 minutes and then centrifuged at 8000 rpm at 150° F. The degummed material is also encompassed by the phrase "RED OIL".

The degummed oil (sea cucumber gut lipid fraction) was first pretreated with 0.5% silica gel, heated to 180° F. and then filtered out using 6 micron filter paper. The recovery of the color was conducted by adding 5 percent bleaching clay to the pretreated oil. The oil was heated to 220° F. for 20 minutes at 28 inches Hg of vacuum. The resulting oil (34 pounds) was light yellow color and most of the pigment was adsorbed in the bleaching clay. This fraction is designated GOLD OIL. The resulting clay was then extracted with acetone 1:2 (w:w) clay to solvent ratio and washed twice. The resulting solution was then desolventized in a Luwa evaporator at 90° C. and 29 inches Hg vacuum and 8 pounds of red lipid fraction concentrate was recovered.

The process resulted in three materials: a yellow/gold oil (GOLD OIL); a concentrated red carotenoid-bearing lipid fraction; and a dry protein powder without lipids. The yellow lipid fraction (GOLD OIL) was incorporated into a topical cosmetic and an oral "nutraceutical" marine "Omega 3 lipid" test product for experimental use. The red concentrated lipid fraction was incorporated into an ornamental fish diet for one month to determine the effectiveness of the carotenoid-bearing lipid at producing suitable color to such fish.

Angiogenesis Inhibition in Chicken Embryos with RED OIL

1 μg of RED OIL was placed on each of 6 methylcellulose discs, ¼ inch in diameter with a micropipette and allowed to dry. The discs were placed onto six 10-day old chick embryo chorioallantoic membranes. and hydrocortisone/lieparin impregnated discs were also placed onto control membranes of another six eggs as described by Knighton et al. (1977). The RED OIL treated membranes showed almost complete inhibition of vascular growth and were more effective in inhibiting neovascularization than the "positive controls" using heparin and lydroconisone. This assay is an in vivo assay and is thought to be indicative of clinical utility of compounds designed to inhibit tumor growth through inhibition of a tumor's blood supply (Knighton et al., 1977).

Adjuvant Induced Arthritis Assay in Rats with RED OIL

RED OIL produced from *Cucumaria frondosa* sea cucumber intestines and body-wall tissue by hexane extraction from dried material as described above, hydrocortisone, and phenylbutazone were used in an adjuvant arthritis model in rats to study their anti-inflammatory effects (Winter and Nuss, 1966; Glenn, 1966; Langford et al., 1972).

The adjuvant arthritis model developed using rats has been shown to be useful in screening compounds that may be useful in the treatment of rheumatoid arthritis in man. The adjuvant induced arthritis responds to both steroids and non-steroids. The degree of inflammation can be assessed by either measuring the increase in paw weight and/or the paw volume.

Methods

Rats weighing between 160–180 g were purchased from B&K Universal, Inc., Kent, Wash. 98032. They were male: Sprague-Dawley. The animals were kept individually in stainless steel cages with free access to water and feed. The light cycle was kept at 12 hours light and 12 hours dark. The temperature was maintained at 22±3° C. and relative humidity was maintained at 40 to 70%. The feed was Harlan Teklan Rodent Diet.

Test Articles

The test materials were suspended in de-ionized water at the doses indicated below. All volumes gavaged were 2 mL.

| Test Material | Lot# | Dose, mg/kg body weight |
| --- | --- | --- |
| De-ionized water | 12/4/98 | 2 mL |
| Hydrocortisone | Spectrum, Lot# HH325 | 10 |
| Phenylbutazone | Sigma, Lot# 15H0063 | 10 |
| RED OIL | Coastside Research | 10 |

Experimental Design

Male Sprague-Dawley rats (160–180 g) were sensitized by injecting Freund's Complete Adjuvant(0.5% suspension of killed mycobacterium tuberculosis (H37RA, Difco in mineral oil)). 0.05 ml, was administered intradermally at a plantar site on the right hind leg of each rat.

The test materials were given orally (by gavage) in 0.5% methylcellulose and given once per day for 7 days. The administration was started the day after sensitization.

The paw weights for each group in each test run were averaged. Activity was calculated as follows: ((Mean paw weights of controls—Mean paw weights of test group)/(Mean paw weights of test group))×100=% Anti-inflammatory Response.

Results and Discussion

The anti-inflammatory response results are presented in Table 2. The anti-inflammatory response is the difference in the mean paw weight of the rat paw treated with Freund's adjuvant compared to the untreated paw. In this study, the hydrocortisone control gave an anti-inflammatory response of 59.0% and phenylbutazone gave a response of 155.3% These two compounds are the positive control. The RED OIL gave an anti-inflammatory response of 158.6% in this assay.

TABLE 2

| | | % Anti-inflammatory Response Based on Mean Paw Volume Decrease | | |
| --- | --- | --- | --- | --- |
| Group | Number of rats | Treatment | Mean Paw Wt., gm | % Anti-inflammatory Response |
| I | 6 | Control, water | 0.97 | 0 |
| II | 6 | Hydrocortisone 10 mg/kg | 0.61 | 59.0 |
| III | 6 | Phenylbutazone, 10 mg/kg | 0.38 | 155.3 |
| IV | 6 | RED OIL, 10 mg/kg | 0.375 | 158.6 |

GOLD OIL was subsequently assayed to determine the inflammation inhibitory activity of the oil in mouse ear edema.

Mouse-ear Edema Model

Figure 7:
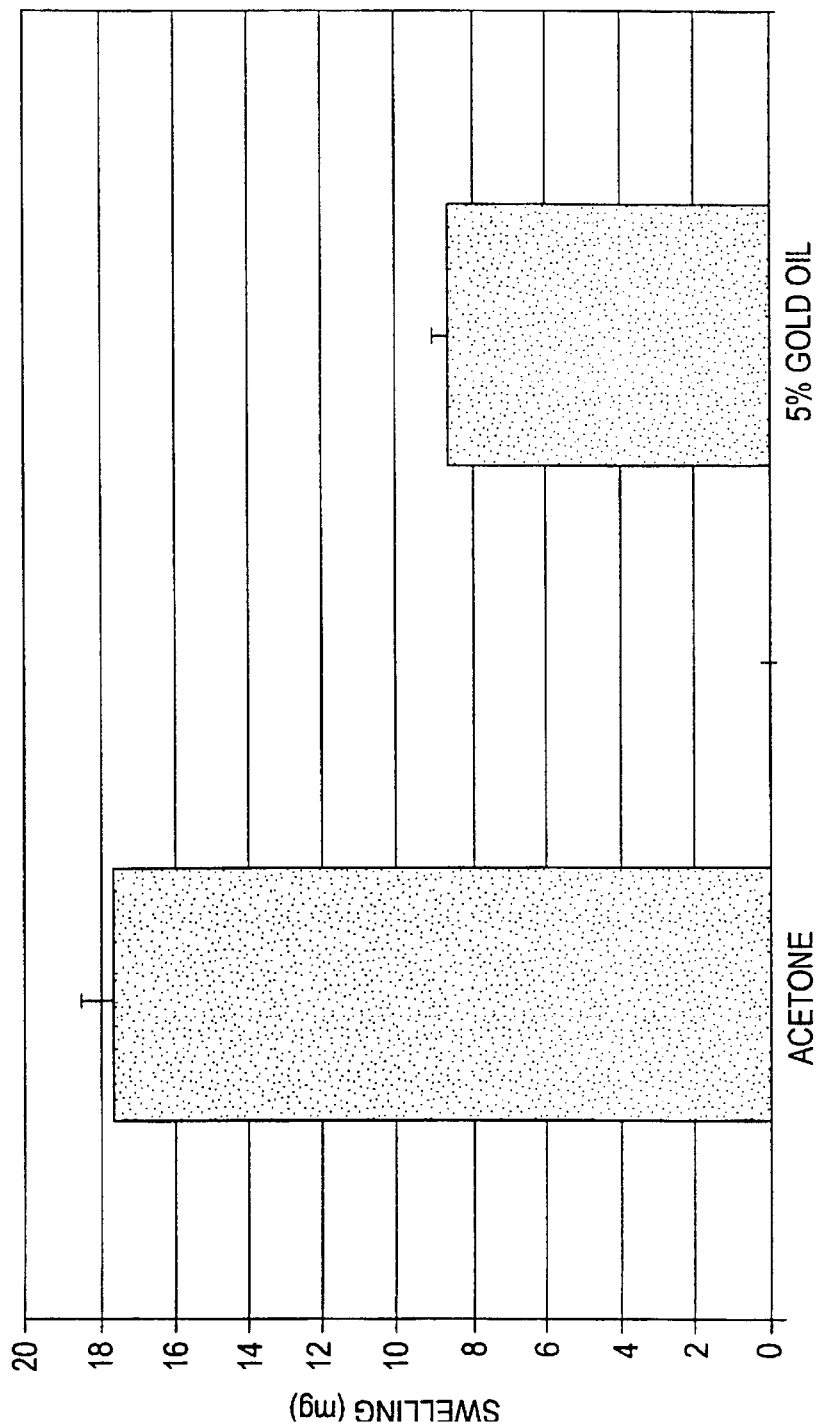
FIG. 7 shows the effect of 5% GOLD OIL on mouse ears challenged with croton oil, compared to acetone control.

Croton-oil, which contains a variety of phorbol esters, and arachidonic acid (AA) are standard inducers of inflammation in mouse ears when applied topically. Multiple topical applications of arachidonic acid to mouse cars induce inflammatory and proliferative changes (Doherty et al., 1988). Phorbol esters, especially phorbol myristyl acetate (PMA), activate one or more isozymes of the ubiquitous membrane receptor, protein kinase C (PKC), which in turn initiates several metabolic cascades leading to inflammation (Castagna et al., 1982). AA is a substrate for one of these cascades, leading to prostaglandin and leukotriene production, both of which are inflammatory. Inhibition of such inflammation by a putative bioactive agent is considered a generalized indicator of potential pharmacologic activity. Weanling, male Balb/C mice were purchased from B&K Universal, Kent. Wash. and maintained in the laboratory for one day prior to entering the experiment. At t=0, the ventral side of both ears of each mouse was challenged topically with 10 μL of 10% croton oil in acetone (n=12 cars) or 5% GOLD OIL dissolved in acetone (n=8 ears). The animals were sacrificed by cervical dislocation at t=24 hrs, the cars removed, and a biopsy taken from each car with an 8 mm punch. The biopsy was immediately weighed on a 4-place balance. Results are given in FIG. 7. The GOLD OIL produced a 52% reduction (p<0.05, Wilcoxin Rank Sum test) in swelling compared to acetone-only treated cars and 50% compared to untreated ears.

Figure 8:
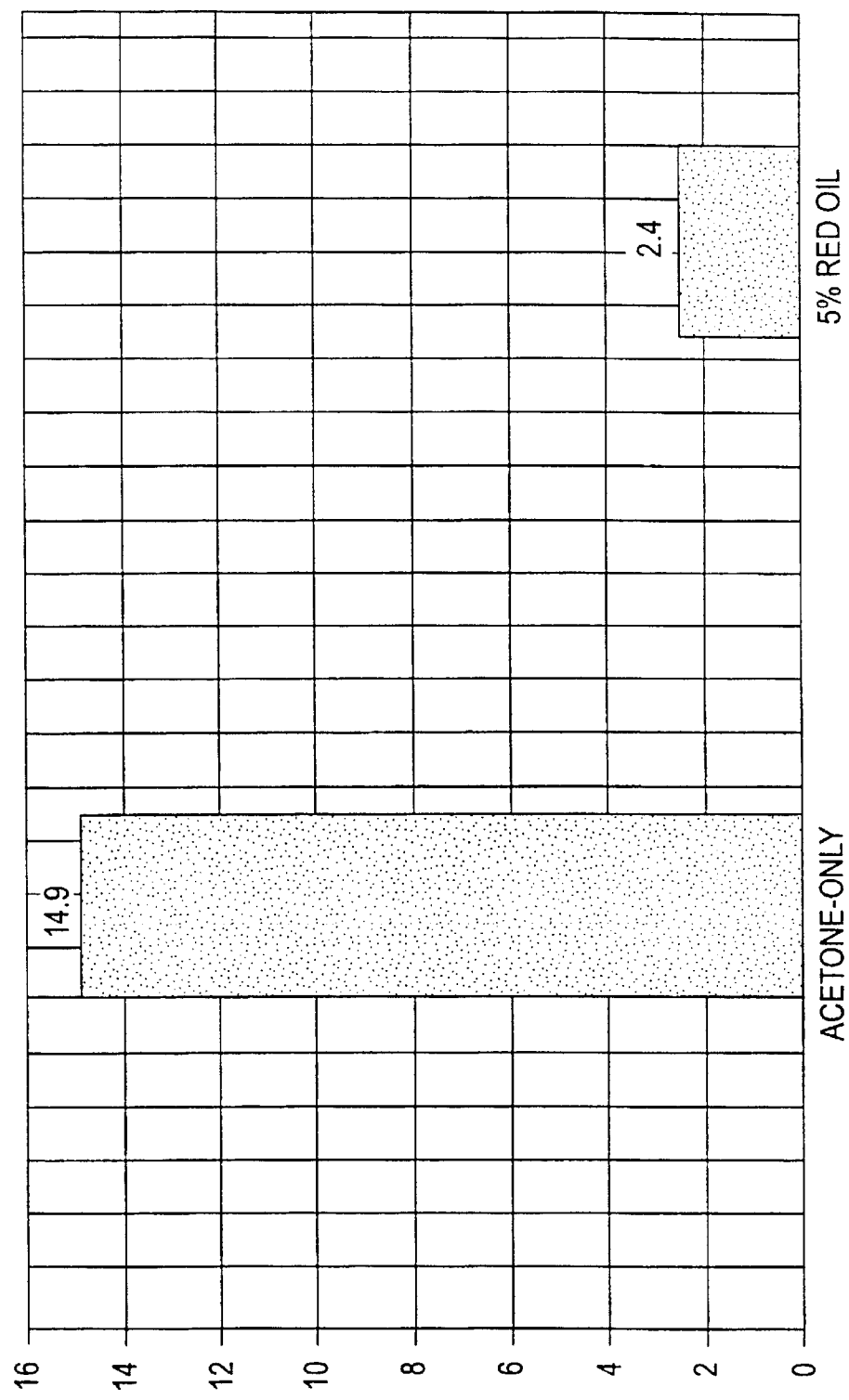
FIG. 8 shows the effect of RED OIL on mouse cars challenged with croton oil compared to acetone control.

RED OIL was assayed to determine the inflammation inhibitory activity of the oil in croton oil initiated mouse car edema as described in the example above. At the same dosages topically, the RED OIL produced an 85% inhibition in swelling compared to acetone-only treated ears. The results are shown in FIG. 8.

5-Tipoxygenase Assay 5-lipoxygenase (5-LO) is a key enzyme in the metabolism of arachidonic acid (AA) to leukotriene $B_4$ ($LTB_4$) and hydroxyeicosatetraenoic acid (5-HETE) it a wide variety of cells. including polymorphonuclear (PMN) leukocytes (Henderson, 1994) and has recently been linked to prostate and other cancers (Ghosh and Myers, 1997). $LTB_4$ is a chemotaxic signaling agent involved in the migration of PMNs from the blood stream to sites of tissue injury, which is a hallmark of the inflammatory response. Human PMNs isolated by standard procedures from a normal volunteer were prewarmed to 37° C. and, at time=0, 10 μL of test compounds suspended in methanol by sonication, or methanol alone, were added to 1 mL of the PMN suspension. At t=10 min, 5 mL of 2 mM AA were added to each suspension as the 5-LO substrate. At t=14 min, the calcium ionophore A23187 (5 mL, 1 mM) was added to activate the enzyme. The reaction was terminated at t=19 minutes by 100 μL of 100 mM citric acid, maintaining a pH of 3.0. Prostaglandin $B_2$ and 15-HETE were added as internal standards for high pressure liquid chromatography (HPLC) quantification of LTB, and 5-HETE, respectively. Metabolites and standards were extracted from the suspension with chloroform/methanol (7:3). The chloroform phase was evaporated and reconstituted in the mobile phase of HPLC elution. Metabolites were detected by ultraviolet light and quantified against standard curves.

A statistically significant and GOLD OIL dose-dependent reduction in PMN production of $LTB_4$, two of its isomers, and 5-HETE are evident in the data presented in FIG. 2. That these results were due to factors other than cellular toxicity is suggested by the observation that exposure of cells to 1:100 and 1:1000 GOLD OIL dilutions for 10 minutes produced 85% and 94% cell viability, respectively. Viability was determined by trypan blue exclusion method as is well known to those skilled in the arts.

HPLC Fractions of RED OIL

RED OIL was fractionated by analytical high pressure liquid chromatography into 18 separate fractions in an E. Merck Si 60 column, 5 μm, 250×4.6 mm with a linear gradient over 30 minutes from 100% hexane to 30% iso-propanol. Flow was 2.0 mL/minute. No fractions were collected for the first two minutes. Fractions were collected at two minute intervals thereafter. All fractions sequestered were submitted to an assay to detect inhibitory activity in the 5 lipoxygenase pathway in human neutrophils as described in previous sections. It was found that fractions 7 and 8 which would have included peaks between 14 and 18 minutes, were active in inhibiting leukotriene $B_4$, 6-trans-leukotriene $B_4$ and 6-trats-12-epi-leukotriene $B_4$ and 5-1-HETE (5(S)-hydroxy-(E,Z,Z,Z)-6,8,11,14-cicosatetraenoic acid).

12-MHTE Assays

RED OIL and GOLD OIL were assayed by the method similar to the assay for 5-lipoxygenase by using human platelets. Polymorphonuclear leukocytes were mixed, challenged with A23187, and 12-HETE production was measured by high pressure liquid chromatography (HPLC). Addition of a 1:10,000 dilution of RED OIL to the reaction yielded 12-HETE levels that were 65% that of methanolic controls, while A 1:1000 dilution of GOLD OIL yielded levels that were 46% of controls.

Mast-cell Degranulation

Weanling male Balb/c mice were treated with GOLD OIL dissolved in hexane at 24 hrs, 12 hrs, and 5 minutes before challenge as well as 5 minutes and 20 minutes after challenge. Ears were challenged with 20 μL of 10% croton oil in acetone applied to both sides of the pinna. 8-millimeter punch biopsies were taken from each ear 6 hours after challenge, weighed and preserved in formalin for histologic analysis. Three 5 micron slices were removed at one-third intervals through the paraffin-embedded biopsy and stained with toluidine blue. which is specific for histamine-containing granules. The middle section as well as those that showed degranulation were counted. Results are provided in Table 3.

TABLE 3

Degranulation of mouse-ear mast cells from topical challenge with croton oil

| Treatment | % Degranulated |
|---|---|
| Vehicle (hexane) | 72.4 (2.2) |
| 10% GOLD OIL | 20.4 (3.5) |
| 10% Paraffin Oil | 66.4 (3.0) |

Ears were treated prophylactically for 24 hours plus two post challenge treatments as described. Data are given as mean (+/− standard error of the mean, n=4 cars) percent of mast cells degranulated.

Lymphocyte Proliferation Assay

The effect of the GOLD OIL and RED OIL on lymphocyte proliferation was assessed by the tritiated ($^3$H)-thymidine uptake assay. Peripheral blood was obtained by venipuncture either from human volunteers or from sheep and the peripheral blood mononuclear cells (PBMNC) were separated from red blood cells and granulocytes by Ficoll density gradient centrifugation. After centrifugation, the PBMNC were aspirated, washed in PMS and resuspended in the medium (RPMI containing 10% fetal calfserum (FCS) and 2 mM glutamine). The PBMNC were adjusted to a density of $2 \times 10^6$/mL and 100 μL aliquots ($2 \times 10^5$ cells) were pipetted into wells of a 96-well round-bottomed plate. Each experimental group consisted of replicates of 5 wells. The cells were incubated for 24 hours in the presence of either GOLD OIL or RED OIL in a range of dilutions. Dilution of oils was made as follows: A micelle suspension of the oils was made in absolute ethanol to a concentration of 5% (v/v). This 5% solution of oil was further diluted in RPMI medium containing 10% FCS to yield a range of dilutions (0.0062, 0.0125, 0.025, 0.05, 0.1% v/v). Each dilution step was vigorously mixed to maintain the oil in suspension.

In control wells, cells were cultured without any oil. After 24 hours of incubation 1 μCurie of $^3$H-thymidine was added to each well containing the lymphocytes and was incubated for a further 18 hours to allow the incorporation of $^3$H-thymidine into the replicating DNA of the lymphocytes. Cells were harvested from the 96-well plates onto glass-fiber filters which entrap radioactively labeled DNA. The filter containing the harvested cells was then counted for $^3$H using a scintillation counter, as per standard procedures known to those skilled in the arts.

In addition, the mitogen Concanavalin A (Con A) was added to lymphocytes at a concentration of 10 μg/mL. The effect of the oils on the mitogenic stimulation was evaluated by co-incubation of the oils with Con A. Concanavalin A is a lectin obtained from *Canavalia esnsiformis* (Jack Bean) which has affinity for alpha-D-mannosyl and alplia-D-glucosyl residues. Con A exhibits mitogenic activity which is dependent on the ability of the molecule to form aggregates and requires calcium and/or manganese ions.

Results and Discussion

The untreated PBMNC preparation showed low baseline incorporation of $^3$H thymidine. However, when PBMNC were stimulated with Con A, these cells demonstrated increased proliferation as indicated by the increased $^3$H thymidine uptake compared to their baseline values. Furthermore, when either GOLD OIL or RED OIL was co-incubated with Con A. there was an observed dose response inhibition of proliferation as indicated by the reduction in $^3$H-thymidine incorporation by PBMNC. Con A-stimulated human PBMNC proliferation was inhibited between 71% to 12% in a dilution range between 0.1% to 0.025% of GOLD OIL and sheep PBMNC were inhibited by 100% to 57% in the same dilution range. The inhibitory effects of the RED OIL showed a similar trend to that observed with the GOLD OIL. RED OIL produced inhibition of 85% at dilution of 0.1% in human PBMNC and in sheep PBMNC showed an inhibition of 95% at 0.1% and a 56% inhibition at 0.05%.

Mixed Lymphocyte Reaction with RED OIL

The mixed lymphocyte reaction (MLR) is an in vitro assay of lymphocyte proliferation mediated by the alloreactivity of lymphocytes from two unrelated individuals. This proliferative response is measured by the uptake of tritiated thymidine. Essentially, in the MLR, the antigen presenting cells (APC) from one individual present allo-peptides via the MHC molecules to T cell receptors on T cells of the second individual. This reaction is termed Signal 1. Subsequent to Signal 1, co-stimulation is mediated (Signal 2) by the interaction of cell adhesion molecules between the T cell and the APC (e.g., CD28-B7) which lead to T cell activation and proliferation. Therefore, the MLR is an it vitro representation of the alloreactivity that ensues in both host-versus graft disease (bone-marrow transplantation rejection) and graft versus host disease (organ transplantation rejection). This assay has been widely used clinically to predict alloreactivity and also experimentally to screen potential immunosuppressive agents. RED OIL was compared with Cyclosporin A which is currently used world-wide as an immunosuppressive agent.

Procedure for MLR with RED OIL

An MLR using cells from two unrelated donors can be studied on the basis that the two cell populations are responding concurrently to each other (i.e., two-way MLR). Peripheral blood was obtained by venipuncture from two unrelated human volunteers and peripheral blood mononuclear cells (PBMNC) were separated from red blood cells and granulocytes by Ficoll density gradient centrifugation. After centrifugation. PBMNCs were aspirated, washed in PBS and resuspended in RPMI containing 10% human AB scra and 2 mM glutamine. Three MLRs were performed with PBMNCs derived from 3 pairs of unrelated individuals and were found to be statistically similar to each other.

In a typical experiment PBMNCs from two unrelated individuals were adjusted to a density of $2 \times 10^5$ cells/mL and 50 μL aliquots (i.e., $1 \times 10^5$ cells) from each were mixed into wells 96-well round bottomed plate. Each experimental group consisted of replicates of 5 wells. The cells were incubated in the presence of either Cyclosporin A or RED OIL in a range of dilutions. The dilutions were prepared as follows: A micelle suspension of the RED OIL was made in absolute ethanol to a concentration of 5% (v/v). This 5% solution of oil was further diluted in RPMI medium containing 10% human AB sera to yield a range of dilutions (0.0062, 0.0125, 0.025,0.05 and 0.01% v/v). Each dilution step was vigorously mixed to maintain the oil in suspension. Cyclosporin A was diluted in tissue culture medium to give a final concentration of 100 ng/mL and 500 ng/mL.

In control wells (untreated), cells were cultured without any agents. After 96 hours of incubation 1 μCurie of $^3$H-thymidine was added to each well containing the mixed lymphocytes and was incubated for a further 18 hours to allow the incorporation of $^3$H-thymidine into the replicating DNA of the lymphocytes. Cells were harvested from the 96-well plates onto glass-fiber filters which entrap radioactively labeled DNA. The filter containing the harvested cells was then counted for $^3$H using a scintillation counter.

Results of MLR with RED OIL

The untreated MLR preparation showed high baseline incorporation of $^3$H-thymidine which is indicative of the alloreactivity between the two unrelated lymphocyte populations.

In the presence of Cyclosporin A at both 100 nanograms per mL and 500 nanograms per mL, decreased proliferation as indicated by the reduced $^3$H-thymidine uptake was observed. The inhibition was expressed as a percentage of the untreated MLR. The Cyclosporin A inhibition of the MLR ranged from 37–75% at 100 ng/mL and 81–90% at 500 ng/mL. This is consistent with the known immunosuppressive properties of Cyclosporin A. Cyclosporin A interacts with immunophilins and prevents the nuclear translocation of the transcription factor NF-AT which is important for the translocation of interleukin-2 (IL-2. a T-cell growth factor).

RED OIL also showed a dose-dependent inhibition of the MLR as indicated by the reduction in $^3$H-thymidine incorporation. At a dilution of 0.025% the inhibition of the MLR was in the range of 40–52% in the three assays performed and at a dilution of 0.05% the inhibition ranged from 82–98%. Cell viability determined by trypan blue exclusion, as is known to the arts, showed that dilution ranges between 0.025% and 0.05% had cell viability between 70–99%, and indicates a potential lack of toxicity of the RED OIL in those dilutions. Dilutions of the RED OIL at 0.1% showed decreased cell viability.

Compounds exhibiting immunosuppression as evidenced in these assays have been shown to have useful therapeutic properties. Therefore it is an object of the present invention that the RED OIL and GOLD OIL be incorporated into pharmaceutical compounds having immunomodulatory activities. Immunomodulator compounds may be immunostimulants for building up immunities to, or initiating healing from, certain diseases and disorders. Conversely, immunomodulators may be immunoinhibitors or immunosuppressors for preventing undesirable immunoreaction of the body to foreign materials, or to prevent or ameliorate autoimmune reactions or diseases.

Immunomodulators have been found to be useful for treating systemic autoimmune diseases, such as lupus erythematosus and diabetes, as well as immunodeficiency diseases. Further, immunomodulators may be useful for immunotherapy of cancer or to prevent rejection of foreign organs or other tissues in transplants, e.g., kidney, lung, heart, or bone marrow (Grover et al., 1997).

Various immunomodulator compounds have been discovered, including FK506, muramylic acid dipeptide derivatives, levamisole, niridazole, oxysuran, flagyl, and others from groups of interferons, interleukins, leukotrienes, corticosteroids, and cyclosporins. Many of these compounds have been found, however, to have undesirable side effects and/or high toxicity. New immunomodulator compounds are therefore needed to provide a wider range of immunomodulator function for specific areas with a minimum of undesirable side effects (Ishida et at., 1997).

Immunomodulation is thus of prime importance to man, and considerable research has been devoted to immunomodulatory measures. Additional methods and compositions are needed.

The present invention has as an object, utilization of the oil of sea cucumbers as a source material and supplemented by synthetic production methods if they become available. The present invention has added to the arsenal of immunomodulatory compounds by the discovery of novel, useful immunomodulators, including compounds able to be isolated from extracts of marine sea cucumbers of any species.

Therefore. an additional object of the present invention pertains to the immunosuppressive use of the RED OIL and GOLD OIL isolated from sea cucumber tissues, and various derivatives and analogs of these compounds. These compounds can be used to reduce, suppress, inhibit, or prevent unwanted immune responses. Advantageously, this immunosuppression can be achieved without cytotoxicity. Therefore, these compounds are useful for treatments of humans or animals requiring immunosuppression. Examples of such situations include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents. The subject invention further pertains to pharmaceutical compositions containing these compounds.

The intended use is for immune reactions (in vivo in vitro) that require modulation via T cell activity. One aspect of the subject invention concerns human in vivo suppression of T cell response, e.g., transplantation and autoimmunity. Since cyclosporin is currently utilized in the medical arts for the suppression of psoriasis, it is an object of the present invention to incorporate the RED OILs or GOLD OILs into the ointments and topical applications described herein for the modulation of immune responses in the skin of psoriasis patients. The beneficial responses obtained by this invention with psoriasis patients, as described in other sections of this invention, may well be resultant of localized dermal immunosuppression of T cells and/or B cells in the patient.

The dosage administered will be dependent upon the immunomodulatory response desired, the type of host involved; its age, health, weight, kind of concurrent treatment, if any; frequency of treatment: therapeutic ratio and like considerations. Advantageously, daily dosage levels of the administered active ingredients can be, for example, dermal −1 to about 500 mg/kg; oral −0.01 to 200 mg/kg; intranasal −0.01 to about 100 mg/kg; and aerosol −0.01 to about 50 mg/kg of animal body weight.

Expressed in terms of concentration, the active ingredient of the invention can be present in the new compositions for localized use dermally, intranasally, bronchially, intramuscularly, intravaginally, intravenously, or orally in a concentration of from about 0.01 to about 50% W/w of the composition, and especially from about 0.01 to about 30% w/w of the composition.

Compounds useful according to the subject invention can be isolated by various techniques as described herein. It will be apparent to those skilled in the art that the examples involve use of materials and reagents that are commercially available from known sources, e.g., chemical supply houses. No details are given respecting them other than details presented herein for the incorporation of the subject oils into various capsules, ointments, lotions, soaps and shampoo.

Discussion of Variables

The scope of the invention is not limited by the specific examples and suggested procedures and uses related herein since modifications can be made within such scope from the general information provided by this specification to those skilled in the art.

The following formulations exemplify some of the dosage forms of the compositions of this invention. In each, the term 'active compound' refers to lipid compounds derived from the tissues of sea cucumbers of any species, purified or not; fractionated or not.

Oral Administration

RED OIL and GOLD OIL as described herein have been encapsulated into prototype 'soft-gel' capsules as are well known in the nutraceutical industry. Oils of the present invention are stabilized with mixed tocopherols such as are known to the industry. RED OIL, produced by the hexane extraction of dried, stabilized sea cucumber gut material from *Cucumaria frondosa*, was de-gummed by methods known to those skilled in the arts, and stabilized by the addition of 1% of mixed tocopherols (COVI-OX-T70 from Henkel Corporation, Pa.) to prevent oxidation. Prototype soft-gels were produced in the amount of 1,000 pieces of 500 milligrams of RED OIL of the present invention. GOLD OIL, derived from RED OIL as described herein, was also incorporated into prototype soft-gel capsules for experimental use.

GOLD OIL and RED OIL have also been incorporated into orange juice at 1:5 (v:v) with the addition of lecithin to enhance solubilization of the lipids with the aqueous phases of the orange juice.

Topical Administration

RED OIL and GOLD OIL of the present invention are formulated into the following forms which exemplify some of the forms in which the anti-psoriatic agents may be employed.

Example A

| Ointment | |
| --- | --- |
| Ingredient | mg |
| Active compound | 1–20 |
| Benzyl Alcohol, NF | 20.0 |
| Almond Oil or other oil | 30.0 |
| White Petrolatum, USP | to make 1.0 g total |

Method of Manufacture: Combine oil ingredients slowly to alcohol ingredients at 140° F. while stirring.

Example B

| Cream | |
| --- | --- |
| Ingredient | mg |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water | to make 1.0 g total |

Method of Manufacture: Heat the stearic acid, glyceryl, monostearate and polyethylene sorbitan monopalmitate to 70° C. In a separate vessel, dissolve sorbitol solution, benzyl alcohol, water, and half quantity of propylene glycol and heat to 70° C. Add the aqueous phase to oil phase with high speed stirring. Dissolve the active compound in remaining quantity of propylene glycol and add to the above emulsion when the temperature of emulsion is 37–40° C. Mix uniformly with stirring and cool to room temperature.

Example C

Nasal Inhalant

For administration as an oral or nasal inhalant, known inert liquids, such as propylene glycol, may be used as vehicles. It may also be administered from a pressurized inhaler in known propellants, such as trichlorofluromethanie and dichlorodifluoromethiane. with the optional presence of dispersing agents, all as is well known in the art.

Example D

| Gel | |
| --- | --- |
| Ingredient | mg |
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | to make 1.0 g total |

Method of Manufacture: Prepare a 1% solution of the sodium hydroxide in propylene glycol. Add approximately one half the remaining propylene glycol and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and mix until a thick gel forms. Dissolve the active compound in the remaining propylene glycol and add to the gel slowly as the gel is continuously mixed.

Example E

| Lotion | |
| --- | --- |
| Ingredient | mg |
| Active Compound | 1.0–20.0 |
| Carbomer 940 | 3.0 |
| Sodium hydroxide (charged as 4% w/w aqueous solution) | 0.05 |
| Isopropyl Alcohol | 40.0 |
| Purified water | to make 1.0 g total |

Method of Manufacture: Prepare a 4% solution of sodium hydroxide in water. Heat the purified water to 60° C. Add carbomer 940 and mix at high speed until dispersed. Cool the above mixture to room temperature and slowly add sodium hydroxide solution until uniform. Add 80% of the isopropyl alcohol to the above with mixing. Dissolve the active compound in the remaining isopropyl alcohol. Add this to the mixture with stirring. Adjust pH to 5.0 to 5.5 with sodium hydroxide if necessary.

Example F

| Combination Herbal Anti-psoriasis Cream | |
| --- | --- |
| Ingredients | Percentage |
| Active compound | 1–20 |
| Green Tea Concentrate | 1–5 |
| *Boswellia serrata* extract | 1–10 |
| Silymarin | 1–10 |
| fucosylated chondroitin sulfate | 1–20 |
| beeswax | 1–40 |
| turmeric oil | 1–10 |
| occimum sanctum oil | 1–10 |
| ginger alcohol extract | 1–10 |
| water | 1–30 |
| DMSO | 1–5 |
| Emu oil | 1–30 |
| Tea tree oil | 1–5 |

Methods of Manufacture: It is an object of the present invention to provide the basis of a formula in which beneficial agents are synergistically combined which ameliorate a psoriatic condition. It is well known that psoriasis disease is mediated by a number of inflammatory mediators. Angiogenesis is a component of this disease, as is the 12, 15- and 5-lipoxygenase pathway. Complement activation is also a mediator of this disease. It has been shown by the inventor that a salve combining the RED OIL or GOLD OIL as lipoxygenase inhibitor agent; fucosylated chondroitin sulfate, as angiogenesis and complement inhibitor agent, *Boswellia serrata* extract as complement inhibitor agent and green tea extract as dermal anti-oxidant and ornithine decarboxylase inhibitor in a matrix of wax carriers and other herbal preparations, provides an effective topical therapeutic for psoriasis. Ginger extract has been shown to be an inhibitor of ornithine decarboxylase, a co-mediator of psoriatic inflammation. Various percentages of these agents may be combined with emulsifiers and other agents making them suitable for topical application. Percentages of the active agents may vary depending on the patient condition and the level of various symptoms resulting from the various mediators. In other words, a patient with abundance of angiogenic neovascularization may need more of the fucosylated chondroitin sulfate than a patient whose psoriatic plaques exhibit an increased activation of the lipoxygenase pathway. It is thought that a clinician skilled in determination of the various pathways involved in psoriatic plaques will be able to formulate a suitable combination of the agents listed in Example E. For example, serum from psoriatic patients can be assayed for activation of the lipoxygenase pathways in local pustular foci and the Complement Cascade activation of C5a and C3a in pustular lesions can readily be assessed by those skilled in the arts. Mechanism-based targeting of psoriatic symptoms can thus be achieved by clinicians and formulators skilled in the arts. No further details of carriers, emollients or the like need be included herein.

Example G

Six psoriatic patients ranging in age from 34 to 67. and having various forms of the disease, and in various 'flare' conditions at the time of administration, were given a topical ointment of Example F and were to told to self administer for one month, and to report back to the clinician their subjective assessment of the therapeutic effect of the ointment. Five out of the six patients reported 'greatly improved' or 'complete remission' of their psoriatic symptoms.

Three dogs of unknown breeds, suffering from atopic dermatitis and 'hot-spots' of the trunk and tail-back areas, were given the topical application of Example F by their respective owners in an 'uncontrolled' manner ad libidinal for 6 weeks. All three dog owners reported complete clearance of the symptoms in their animals, and a cessation of scratching and biting of the areas under treatment.

Ten men and women between the ages of 46 and 81, suffering from rheumatoid arthritis as self-reported to the clinician, were given oral supplementation of the RED OIL at approximately 2,000 milligrams per day per person for three months. Eight of these persons reported a 'dramatic lessening' of their disease symptoms and an increased range of movement in their arms and legs. One woman of 81 reported complete cessation of pain in her shoulders and wrists.

Three men aged between 50 and 56 were self-treated with a topical compound comprising RED OIL at 9.5% by weight, menthol, dimetlhylsulfoxide (DMSO), emu oil, oil of wintergreen, alcohol and olive oil for testing the pain-relieving capacity of the RED OIL as a topical 'rub-on' pain control formula. After four days of application to painful shoulders, fingers, or knees, two participants claimed anecdotal subjective benefit as being dramatic, and one man claimed subjective benefit as being moderate.

Four women with self-reported osteoarthritis were given 1,500 milligrams twice per day of GOLD OIL in solutions of orange juice and emulsifier for two months. All four reported 'increased benefit' from the compound and three claimed dramatic decrease in overall pain assessment and increased range of movement.

One 19 year old horse of unknown breed and suffering from arthritis related limp in the right front leg was treated on the knee with a gel comprised of 20% RED OIL and similar to Example D herein described. The gel was wrapped and changed daily for two weeks. At the end of two weeks, the horse owner claimed that there was an increased range of motion and decrease of limping.

One dog with veterinarian-diagnosed canine lupus was given 1,000 milligrams of RED OIL daily for six months mixed in its food. Over the course of treatment, the symptoms of the disease abated and the owner was able to greatly decrease the animal's dosage of a prednisone medicine to 1/10th of former levels.

Two persons suffering from common heart-burn (inflammation of the esophagus) were given GOLD OIL emulsified with lecithin, juice and sugar orally in the amount of 2,000 milligrams of GOLD OIL per day in the juice. They claimed that symptoms were abated within two minutes.

One twenty-two year old person suffering from asthma took as a food supplement 1,000 milligrams of RED OIL daily mixed with other food excipients for a period of two and one half months. During that time, she reported decreased need for her conventional inhalant medication and other indications of subjective benefit.

Three adolescent boys with various acne vulgaris lesions on their faces were administered RED OIL at 1,000 milligrams per day mixed into orange juice and lecithin for 1 month. They all reported subjective benefit from the RED OIL as evidenced anecdotally by decreased eruptions of their conditions.

Anti-cancer Assays

RED OIL and GOLD OIL and various thin-layer chromatographic fractions have been tested against human cancer cell lines in vitro. Materials were initially dissolved in dimethyl sulfoxide and then diluted in tissue culture media. Aliquots of 23 µg/mL were then applied to PC3 (human prostate), MCF7 (human breast adenocarcinoma), HT29 (human colon adenocarcinoma) or BRO (human melanoma) cell lines. These fractions mediated inhibition of cell growth relative to untreated control cells as assessed after 72 hr by the MTT viable dye method as is commonly used by those skilled in the arts. In all cell lines, RED OIL and the various fractions were able to inhibit cell growth in a concentration dependent manner. One such fraction isolated from sea cucumber lipid phase by the method of Findlay et al. (1983b), plastochromanol-8, was considered to be promising in that values of 20–50 µg/mL were determined as $IC_{50}$ values (that concentration inhibiting 50% of cell growth). Plastochromanol-8 was also assayed in the 5-Lipoxygenase assays described above and was shown to be a dramatic inhibitor of 5-Lipoxygenase, $LTB_4$ and several isomers of the enzyme. Plastochromanol-8 was also shown to be inhibitory of the 12-Lipoxygenase pathway in human platelets.

Plastochromanol-8 Data

In a leukotriene activation assay showing the effect of plastochromanol-8 on leukotriene synthesis expressed as a percentage of a methanol control in human neutrophils, by the method of Betts (1997), plastochromanol-8 inhibited activation of 5-HETE by approximately 60 percent, $LTB_4$ by approximately 40 percent, and two of the 6-trans isomers of $LTB_4$ (6-trans-leukotriene $B_4$ and 6-trans-12-epileukotriene $B_4$), by 75%. In a related assay of the effect of plastochromanol-8 on leukotriene synthesis expressed as leukotriene synthesis per $10^6$ PMN, plastochromanol-8 inhibited the production of 5-HETE by approximately 75%, $LTB_4$ by 50%, and the two trans-6 isomers of $LTB_4$ by approximately 80%. In similar assays with human platelets, plastochromanol-8 inhibited 12-HETE synthesis by approximately 80%.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Betts H (1997). *Inflammopharmacology* 5:237–246.
Bullock E and Dawson C J (1970). *Comp. Biochem. Physiol.* 34:799.
Castagna M. et al. (1982). *J. Biol Chem.* 257:7847–7851.
Chen Y Q, et al. (1994). *Cancer. Res.* 54:1574–1579.
DeLuca P, et al. (1995). *Rheum. Dis. Clin. North. Am.* 21:759–777.
Doherty N S. et al. (1988). *J Invest. Dermatol.* 91:298–302.
Findlay J A, et al. (1983a). *Marine Chemistry* 12:228.
Findlay J, et al. (1983b). *J. Nat. Prod.* 47:334–340.
Gao X, et al. (1995). *Urology* 46:227–237.
Ghosh J and Myers C E (1997). *Biochem. Biophys. Res. Commun.* 235:418–423.
Glenn E M (1966). *Am. J. Vet. Res.* 27:339–352.
Grover F L, et al. (1997). *Am. J. Surg.* 173:523–533.
Henderson W R (1994). *Ann. Intern. Med.* 121:648–697.
Hofmanova J, et al. (1996). *Gen. Physiol. Biophys.* 15:317–331.
Honn K V, et al. (1994). *Cancer Metastasis Rev.* 13:365–96.
Honn K V, et al. (1992). *Prostaglandins* 44:413–429.
Hussey H J and Tisdale M J (1996). *Br. J. Cancer* 74:683–687.
Ishida H, et al. (1997). *Toxicology* 12: 167–175.
Knighton D, et al. (1977). *J. Cancer* 2:347–355.
Konig G M and Wright A D (1995). *Planta Medica* 62:193–211.
Langford F D, et al. (1972). *J. Pharm. Sci.* 61:75–78.
Liu B, et al. (1994). *Lab. Invest.* 70:314–323.
Matsuno T, et al. (1995). *Comp. Biochem. Physiol.* B 11B:597–605.
Meyers S and Chen N (1982). *Journal of Food Science* 47:345–348.
Miyamoto T, et al. (1990). *Liebigs Ann. Chem.* 33:453–460.
Moody T W, et al. (1998). *Exp. Lung Res.* 24:617–28.
Tsushima M. et al. (1996). *J. Nat. Prod.* 59:30–34.
Winter C A and Nuss G W (1966). *Arthritis & Rheumatism* 9:394–404.
U.S. Pat. No. 4,495,207
U.S. Pat. No. 4,505,963
U.S. Pat. No. 4,692,280
U.S. Pat. No. 5,519,010
U.S. Pat. No. 5,770,205

What is claimed is:

1. A product comprising a carotenoid-bearing lipid wherein said product is isolated from dried sea cucumber tissue by extraction of said tissue by a solvent.

2. The product of claim 1 wherein said solvent is an organic solvent.

3. The product of claim 1 wherein said tissue is gut tissue.

4. The product of claim 1 wherein said product is isolated by a method comprising the steps of:
   a) separating gut tissue from sea cucumber;
   b) adjusting the pH of said gut tissue to within a range of from about 4 to about 5.5;
   c) drying said gut tissue after having adjusted the pH to within a range of from about 4 to about 5.5;
   d) extracting said gut tissue with said solvent;
   e) separating said solvent from said gut tissue; and
   f) evaporating said solvent;

and optionally can include steps of
   g) degumming;
   h) treating with silica gel;
   i) heating; and
   j) filtering.

5. The product of claim 1 further comprising an antioxidant.

6. The product of claim 1 isolated by a method comprising the steps of:
   a) extracting dried sea cucumber tissue with a solvent to produce an extract;
   b) mixing an adsorbent which binds pigments of said extract; and
   c) removing said adsorbent;
wherein said product consists of what remains after removal of said adsorbent.

7. The product of claim 6 wherein said adsorbent is silicic acid in a column equilibrated with chloroform and said product is removed from said adsorbent by passing chloroform through said column.

8. The product of claim 6 wherein said adsorbent is selected from the group consisting of activated clay, non-activated clay, charcoal and silica.

9. The product of claim 6 further comprising an antioxidant.

10. The product of claim 1 isolated by a method comprising the steps of:
   a) extracting dried sea cucumber tissue with a solvent to produce an extract;
   b) adding an adsorbent which binds pigments of said extract;
   c) removing said adsorbent;
   d) extracting said adsorbent with a solvent;
   e) separating said solvent from said adsorbent; and
   f) removing said solvent thereby leaving said product.

11. The product of claim 10 wherein said adsorbent is selected from the group consisting of activated clay, non-activated clay, charcoal, silicic acid and silica.

12. The product of claim 1 isolated by a method comprising:
   a) extracting dried sea cucumber tissue with a solvent to produce an extract;
   b) distilling said extract; and
   c) collecting a distillation fraction in a condenser of about 25–35° C.

13. The product of claim 12 further comprising an antioxidant.

14. The product of claim 1 isolated by a method comprising:
   a) extracting dried sea cucumber tissue with a solvent to produce an extract;
   b) mixing an adsorbent which binds pigments of said extract;
   c) removing said adsorbent to produce a gold oil;
   d) distilling said gold oil; and
   e) collecting a distillation fraction in a condenser of about 25–35° C.

15. The product of claim 14 further comprising an antioxidant.

16. A product purified from fresh sea cucumber tissue wherein said product is isolated by a method comprising the steps of:

a) separating gut tissue from sea cucumber;

b) adjusting the pH of said gut tissue to within a range of from about 4 to about 5.5;

c) extracting said gut tissue with a solvent;

e) separating said solvent from said gut tissue; and f) removing said solvent;

wherein said product is a carotenoid-bearing lipid material remaining after removal of said solvent.

17. The product of claim 16 wherein said solvent is an organic solvent.

18. A product comprising a lipid wherein said product is prepared by:

a) drying said gut tissue of step (e) of claim 16 to prepare a dried tissue;

b) extracting said dried tissue with a solvent which extracts lipids into a solvent phase;

c) separating said solvent phase from tissue; and d) removing said solvent;

wherein said product is a lipid material remaining after removal of solvent from said solvent phase.

19. The product of claim 18 wherein said solvent is selected from the group consisting of hexane, butane, liquefied propane, alcohols, acetone, chloroform and supercritical carbon dioxide.

20. The product of claim 18 further comprising an antioxidant.

21. An product comprising a proteinaceous material essentially free of lipids wherein said product is prepared by a) drying said gut tissue of step (e) of claim 16 or of step (e) of claim 4 to prepare a dried tissue;

b) extracting said dried tissue with a solvent which extracts lipids into a solvent phase; and c) separating said solvent phase from tissue;

wherein said product is said tissue of step (c).

22. A product comprising a carotenoid-bearing lipid material wherein said product is prepared by placing fresh sea cucumber gut material into hot edible oil then separating said gut material from said oil wherein said product comprises said oil plus lipids extracted from said gut material into said oil.

23. A method to inhibit lipoxygenase activity in a mammal in need of same, by administration of an effective amount of a product selected from the group consisting of said product of claim 1, said product of claim 18 and said product of claim 22.

24. A method to inhibit immune responses in a mammal in need of same by administration of an effective amount of a product selected from the group consisting of said product of claim 1, said product of claim 18 and said product of claim 22, wherein said product is administered at a rate of between 5 mg per kg per day and 500 mg per kg per day.

25. The method of claim 23 wherein said mammal is a human with psoriasis, an arthritic condition or atopic dermatitis.

26. The method of claim 24 wherein said mammal is at risk of transplant rejection.

27. The method of claim 23 wherein the animal is suffering from one or more disease conditions selected from the group consisting of allergy, asthma, arthritis, skin disorders, acne, psoriasis, inflammatory bowel disease, cardiovascular disease, angina, stroke, atopic dermatitis, prostate cancer, lung cancer, skin cancer and digestive tract cancer.

28. The method of claim 24 wherein an animal is suffering from either diabetes, rheumatoid arthritis, osteoarthritis, ankylosing spondylitis, migraine headaches, acne, heartburn, lupus or a cancer and effective agents of the present invention are administered at a dose rate of between 5 mg per kg per day to about 500 mg per kg per day.

29. The method of claim 24 wherein said immune response manifests as acne vulgaris and said mammal is a human.

30. A method to inhibit activity of 5- and 12-lipoxygenases in a mammal by administration of an effective dose of plastochromanol-8, derived from any source or synthetically made, to an animal in need of inhibition of 5- and/or 12-lipoxygenase.

31. The method of claim 30 wherein said mammal is in need of anti-cancer therapy.

32. A composition of matter comprising a product selected from the group consisting of said product of claim 1, said product of claim 18 and said product of claim 22, and further comprising fucosylated chondroitin sulfate, an antioxidant green tea extract, a Ginger alcohol extract, and a Bosiwellia extract as additional Complement inhibitor, wherein said composition of matter is a topical ointment further comprising appropriate excipients suitable for animals and humans.

33. An aquatic diet comprising said product of claim 10.

34. An aquatic diet comprising said product of claim 16.

35. A dry, odorless powder high in essential amino acids and suitable for inclusion in human flit foods, drinks and cosmetics wherein said powder is prepared by a method comprising the 2 steps of:

a) removing lipids from sea cucumber tissue to produce delipidized tissue; and b) hydrolyzing said delipidized tissue.

36. The powder of claim 35 wherein the method for preparing said powder comprises hydrolyzing said delipidized tissue with a basic solution or with an enzyme.

37. The powder of claim 35 prepared by a method comprising the steps of:

a) drying gut tissue of sea cucumber to produce a dried tissue;

b) extracting lipids of said dried tissue with a solvent to produce a de-lipidized tissue;

c) removing said solvent;

d) resuspending said de-lipidized tissue in water;

e) adjusting the pH of said tissue of step (d) to about 12;

f) adjusting the pH of material from step (e) to about 8.5;

g) heating;

h) cooling;

i) centrifuging to remove solids to leave a supernatant phase;

j) adjusting the pH of said supernatant phase to about 3.0 to precipitate protein;

k) separating precipitated protein from solution; and l) drying said precipitated protein;

wherein said precipitated protein is said powder.

38. A method to inhibit angiogenesis in a mammal wherein neovascularization contributes to the pathological condition, by administration of an effective amount of said product of claim 1, said product of claim 18 or said product of claim 22 at between 20 to 500 milligrams per kilogram body weight per day.

39. The method of claim 38 wherein said administration is performed by topically contacting an area of neovascularization.

40. A fraction of the product of claim 1 wherein said fraction is active in inhibiting leukotriene $B_4$, 6-transleukotriene B4 and 6-trans-12-epi-leukontriene $B_4$ and 5-HETE (5(S)-hydroxy-(E,Z,Z,Z)-6,8,11,14-cicosatetraenoic acid.

41. The fraction of claim 40 wherein said fraction is obtained by performing preparative HPLC.

42. A method to inhibit inflammation in a mammal in need of same, by administration of an effective amount of the fraction of claim 40.

43. The method of claim 42 wherein said inflammation results from 5-lipoxygenase activity.

44. A food, drink or cosmetic comprising the powder of claim 35.

45. The composition of claim 4 further comprising an antioxidant.

\* \* \* \* \*

UNITED STATES PATENT AND TRADEMARK OFFICE
CERTIFICATE OF CORRECTION

PATENT NO.   : 6,399,105 B1
DATED        : June 4, 2002
INVENTOR(S)  : Peter Donald Collin It is certified that error appears in the above-identified patent and that said Letters Patent is hereby corrected as shown below:

<u>Title page</u>
Please insert -- Related U.S. Application Data
Continuation-in-part- of application No. 09/010,123, filed on January 21, 1998, now U.S. Patent 6,055,936. --

Signed and Sealed this

Eighth Day of October, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO.     : 6,399,105 B1
DATED          : June 4, 2002
INVENTOR(S)    : Peter Donald Collin It is certified that error appears in the above-identified patent and that said Letters Patent is hereby corrected as shown below:

Column 2,
Line 34, change "a topic" to -- atopic --;
Line 46, change "epidermal." to -- epidermal --;
Line 51, delete "die" and replace with -- the --; and
Line 52, change "5.519,010" to -- 5,519,010 --.

Column 3,
Line 60, change "heart-bum" to -- heart-burn --.

Column 6,
Line 28, change "stercospecific" to -- stereospecific --;
Line 50, change "(Ohosh" to -- (Gosh --; and
Line 65, change "acetohydroxamicacid" with -- acetohydroxamic acid -- and replace "die" with -- the --.

Column 7,
Line 54, change "OTT" to -- OIL --.

Column 9,
Line 13, replace "tile" with -- the --;
Line 24, delete the word "all."

Column 12,
Line 64, change "gutmaterial" to -- gut material --.

Column 13,
Line 67, change "eicosapcntanoic" to -- eicosapentanoic --.

Column 17,
Line 44, change "hydrocortisone/lieparin" to -- hydrocortisone/heparin --; and
Line 50, change "lydroconisone" to -- hydrocortisone --.

Column 19,
Line 15, change "(n=12 cars)" to -- (n = 12 ears) --;
Line 18, change "the cars" to -- the ears --; change "each car" to -- each ear --;
Line 21, change "treated cars" to -- treated ears --; and
Line 24, change "mouse car" to -- mouse ear --; and
Line 29, change "5-Tipoxygenase Assay" to -- 5-Lipoxygenase Assay --.

UNITED STATES PATENT AND TRADEMARK OFFICE
CERTIFICATE OF CORRECTION

PATENT NO. : 6,399,105 B1
DATED : June 4, 2002
INVENTOR(S) : Peter Donald Collin It is certified that error appears in the above-identified patent and that said Letters Patent is hereby corrected as shown below:

Column 20,
Line 12, change "14-cicosatetraenoic" to -- eicosatetraenoic --;
Line 14, change "12 MHTE" to -- 12 HETE --; and
Line 50, change "n=4 cars" to -- n = 4 ears --.

Column 21,
Line 32, change "Con A." to -- Con A, --; and
Line 55, change "it vitro" to -- in vitro --.

Column 22,
Line 7, change "scra" to -- sera --;
Line 13, before "96-well," insert -- of a --.

Column 23,
Lines 55-56, change "(in vivolin vitro)" to -- (in vivo/in vitro) --.

Column 31,
Line 67, change "ostcoarthritis" to -- osteoarthritis. --

Signed and Sealed this

Twenty-seventh Day of April, 2004

JON W. DUDAS
*Acting Director of the United States Patent and Trademark Office*